United States Patent
Manhart

(10) Patent No.: US 12,073,493 B2
(45) Date of Patent: Aug. 27, 2024

(54) METHOD FOR DEFINING A CAPTURE TRAJECTORY

(71) Applicant: Siemens Healthcare GmbH, Erlangen (DE)

(72) Inventor: Michael Manhart, Fuerth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/161,267

(22) Filed: Jan. 30, 2023

(65) Prior Publication Data

US 2023/0245355 A1    Aug. 3, 2023

(30) Foreign Application Priority Data

Jan. 31, 2022 (DE) .................... 10 2022 201 003.5

(51) Int. Cl.
    *G06T 11/00*          (2006.01)
    *A61B 6/00*           (2024.01)
    (Continued)

(52) U.S. Cl.
    CPC .............. *G06T 11/008* (2013.01); *A61B 6/12* (2013.01); *A61B 6/4021* (2013.01); *A61B 6/488* (2013.01);
    (Continued)

(58) Field of Classification Search
    CPC ........... A61B 6/027; A61B 6/032; A61B 6/12; A61B 6/4021; A61B 6/4441; A61B 6/488;
    (Continued)

(56) References Cited

U.S. PATENT DOCUMENTS 6,542,772 B1 *   4/2003   Chance ................ A61B 5/4312
                                                       600/476
10,736,595 B2     8/2020   Dinitto
                        (Continued)

FOREIGN PATENT DOCUMENTS

CN          201242531 Y     5/2009
CN          107752979 A     3/2018
                     (Continued)

OTHER PUBLICATIONS

German Office Action and English translation thereof dated Nov. 10, 2022.

(Continued)

*Primary Examiner* — Kenny A Cese
(74) *Attorney, Agent, or Firm* — Harness, Dickey & Pierce, P.L.C.

(57) ABSTRACT

A computer-implemented method comprises: providing at least two exploratory views; segmenting a first object in the at least two exploratory views to determine first two-dimensional object masks; segmenting the second object in the at least two exploratory views tow determine second two-dimensional object masks; determining a first three-dimensional object mask as a function of the first two-dimensional object masks; determining a second three-dimensional object mask as a function of the second two-dimensional object masks; and determining an overlap of the first object and the second object for at least one capture trajectory as a function of the first three-dimensional object mask and the second three-dimensional object mask.

21 Claims, 8 Drawing Sheets

(51) Int. Cl.
*A61B 6/12* (2006.01)
*A61B 6/40* (2024.01)
*G06T 7/11* (2017.01)
*G06T 7/136* (2017.01)

(52) U.S. Cl.
CPC .............. *A61B 6/5258* (2013.01); *G06T 7/11* (2017.01); *G06T 7/136* (2017.01); *G06T 11/006* (2013.01); *G06T 2200/04* (2013.01); *G06T 2207/10116* (2013.01); *G06T 2207/20021* (2013.01); *G06T 2207/20081* (2013.01); *G06T 2207/30004* (2013.01); *G06T 2207/30241* (2013.01); *G06T 2210/41* (2013.01); *G06T 2211/421* (2013.01)

(58) Field of Classification Search
CPC ........ A61B 6/5258; G06N 20/00; G06N 3/08; G06T 11/006; G06T 11/008; G06T 15/00; G06T 2200/04; G06T 2207/10116; G06T 2207/20021; G06T 2207/20081; G06T 2207/30004; G06T 2207/30241; G06T 2210/41; G06T 2211/421; G06T 7/11; G06T 7/136
USPC ................................................. 382/103, 132
See application file for complete search history.

(56) References Cited

U.S. PATENT DOCUMENTS

| | | | |
|---|---|---|---|
| 2006/0204076 A1* | 9/2006 | Avinash | G06T 11/006 348/42 |
| 2008/0091171 A1* | 4/2008 | Strommer | G06T 7/564 604/528 |
| 2013/0124148 A1* | 5/2013 | Jin | G06T 7/55 703/1 |
| 2015/0029178 A1 | 1/2015 | Claus et al. | |
| 2015/0178917 A1* | 6/2015 | Yang | A61B 6/5258 382/131 |
| 2018/0061090 A1 | 3/2018 | Jerebko et al. | |
| 2018/0098744 A1 | 4/2018 | Bauer | |
| 2018/0357796 A1* | 12/2018 | Bishop | A61B 3/102 |
| 2020/0250820 A1 | 8/2020 | Kunze et al. | |
| 2021/0174502 A1* | 6/2021 | Siewerdsen | A61B 6/4441 |
| 2021/0295542 A1* | 9/2021 | Yan | G06T 7/33 |
| 2021/0321969 A1 | 10/2021 | Manhart | |
| 2021/0401392 A1* | 12/2021 | Bengtsson | A61B 6/5217 |
| 2022/0395230 A1* | 12/2022 | Athanasiou | A61B 5/6876 |

FOREIGN PATENT DOCUMENTS

| | | |
|---|---|---|
| CN | 107928691 A | 4/2018 |
| CN | 111524200 A | 8/2020 |
| CN | 113538330 A | 10/2021 |
| DE | 102020131786 A1 | 6/2021 |
| EP | 3725229 A1 | 10/2020 |

OTHER PUBLICATIONS

German Decision to Grant and English translation thereof dated Mar. 14, 2023.

Meyer, Esther et al. "Normalized metal artifact reduction (NMAR) in computed tomography" Medical Physics, vol. 37, No. 10, pp. 5482-5493, 2010 // DOI: 10.1118/1.3484090.

Wu, P., et al.: Method for metal artifact avoidance in C-Arm cone-beam CT. In: Medical Imaging 2020: Physics of Medical Imaging. SPIE, 2020. S. 522-530.; 2020.

* cited by examiner

METHOD FOR DEFINING A CAPTURE TRAJECTORY

CROSS-REFERENCE TO RELATED APPLICATION(S)

The present application claims priority under 35 U.S.C. § 119 to German Patent Application No. DE 10 2022 201 003.5, filed Jan. 31, 2022, the entire contents of which are incorporated herein by reference.

FIELD

One or more example embodiments of the present invention relate to a method for defining a capture trajectory for recording a first and a second object in a three-dimensional medical image and to a determination system which is configured to carry out the method. One or more example embodiments of the present invention further relate to a training method for providing a first trained function. One or more example embodiments of the present invention further relate to a training method for providing a second trained function. One or more example embodiments of the present invention further relate to a computer program product and to a computer-readable storage medium.

BACKGROUND

A known problem in imaging, in particular in three-dimensional imaging, is that overlapping of different mapped objects or artifacts caused by mapped objects complicates correctly depicting the individual objects in three-dimensional imaging or even renders this impossible. For example, metal artifacts caused by a first object in three-dimensional X-ray imaging can result in it not being possible using three-dimensional imaging to correctly depict a second object which is entirely or partially overlapped by the metal artifact.

In three-dimensional imaging, a plurality of two-dimensional projection captures of an object under examination are typically recorded by way of an imaging system. The two-dimensional projection captures map the object under examination from different angles or capture angles. The plurality of two-dimensional projection captures are typically recorded by the imaging system traveling along a capture trajectory relative to the object under examination. The two-dimensional projection captures are recorded while the capture trajectory is being traveled along.

The object under examination may here for example be at least one part of a human or animal or an inanimate object. The first and the second object are here arranged in the object under examination. The first and the second object are thus likewise mapped in the two-dimensional projection captures.

A three-dimensional image can be reconstructed or determined as a function of the plurality of two-dimensional projection captures. The first object may here overlap the second object in the two-dimensional projection captures in such a manner that the second object cannot be correctly depicted in the three-dimensional image. The overlap may here in particular be brought about or caused by a metal artifact produced by the first object. Hereinafter, the phrase "the first object overlaps the second object" also encompasses the meaning that the artifact produced by the first object overlaps the first object.

A correct depiction of the mapped objects is of great relevance in particular in medical imaging. A correct depiction may be of great relevance or crucial to a diagnosis or treatment. A second object being overlapped by a first object or by an artifact, for example a metal artifact, caused by the first object may result in an incorrect diagnosis. Alternatively or additionally, the second object being overlapped by the first object in a three-dimensional medical image may result in it not being possible to carry out a treatment properly. The treatment may here be for example correct positioning of a stent or arresting a bleed. If the stent or bleed is not correctly mapped in the three-dimensional medical image due to the overlap, it may under certain circumstances be impossible to position the stent correctly or to arrest the bleed in a targeted manner.

Meyer, Esther, et al. "Normalized metal artifact reduction (NMAR) in computer tomography." Medical Physics 37.10 (2010): 5482-5493, for example, describes metal artifact correction for three-dimensional X-ray imaging. However, if the metal artifact produced by the first object overlaps the second object to too great an extent in the two-dimensional projection captures, it may be impossible, despite metal artifact correction, to correctly depict the second object in the reconstruction of the three-dimensional medical image.

German Patent Application No. DE 10 2020 131 786 A1 describes that the capture trajectory can be adapted in such a manner that metal attenuation, for example by the first object, can be minimized. The method is, however, based on the first object which causes the metal attenuation being isotropic, i.e. having a directional dependency in its shape. Moreover, the method merely describes how, in general terms, the influence of metal attenuation of a first object can be reduced without direct reference to a second object. The method does not describe how an overlap of two objects should be taken into account on determination of the capture trajectory.

U.S. Pat. No. 10,736,595 B2 discloses a method for reducing an overlap of a target region in an object under examination by metal artifacts. The metal artifacts are here produced by an object which is arranged outside the object under examination. In particular, the object which produces the metal artifacts is one or more pins which are immobilizing the object under examination. For this purpose, a plurality of first two-dimensional projection captures are firstly recorded along a first capture trajectory, from which the trajectory of the one or more pins can be determined. A second capture trajectory can be determined on the basis of the trajectory of the one or more pins. Projection images which are recorded along the second capture trajectory map an overlap of the one or more pins with the target region which is reduced in comparison with that of the plurality of first two-dimensional projection captures. The target region may here in particular be the second object. A plurality of second two-dimensional projection captures are then recorded along the second capture trajectory. A three-dimensional image of the object under examination including the target region can then be reconstructed or determined as a function of the plurality of second two-dimensional projection captures. Thus, according to the described method, the plurality of first two-dimensional projection images must firstly be recorded along the first capture trajectory in order to determine the second capture trajectory. If the imaging is X-ray imaging, on recording the plurality of first two-dimensional projection captures, a dose is administered to the object under examination which is not directly necessary for generating the final three-dimensional image. Thus, determining the second capture trajectory on the basis of the plurality of first two-dimensional projection captures involves administering a dose which is at least approximately twice that involved in purely recording the three-dimensional image. In addition, the first object is arranged outside the object under examination and can thus readily be repositioned.

SUMMARY

It is an object of one or more example embodiments of the present invention to provide a method which makes it possible to reduce an overlap of two objects in an object under examination on recording a three-dimensional medical image in a manner which is as time-efficient and, if of relevance to the imaging in question, as dose-efficient as possible.

At least said object is achieved by a method for defining a capture trajectory for recording a first and a second object in a three-dimensional medical image, by a determination system for defining a capture trajectory for recording a first object and a second object in a three-dimensional medical image, by a training method for providing a first trained function, by a training method for providing a second trained function, by a computer program product and by a computer-readable storage medium according to one or more example embodiments of the present invention and/or the claims. Advantageous further developments are presented in the following description.

At least one object is achieved according to one or more example embodiments of the present invention as described below both in relation to the claimed devices and in relation to the claimed method. Features, advantages or alternative embodiments mentioned in this connection are likewise also transferable to the other claimed subjects and vice versa. In other words, the substantive claims (e.g. directed to a device) can also be further developed with the features which are described or claimed in connection with a method. The corresponding functional features of the method are here formed by corresponding substantive modules.

The manner in which the object is achieved according to one or more example embodiments of the present invention is furthermore described both in relation to methods and devices for defining a capture trajectory and in relation to methods and devices for providing a first and a second trained function. Features and alternative embodiments of data structures and/or functions in methods and devices for determining can here be applied to analogous data structures and/or functions in methods and devices for adapting/optimizing/training. Analogous data structures may here in particular be characterized by the use of the qualifier "training". Furthermore, the trained functions used in methods and devices for defining a capture trajectory may in particular have been trained or adapted and/or provided by methods for providing the trained function.

One or more example embodiments of the present invention further relate to a computer-implemented method for defining a capture trajectory for recording a first and a second object in a three-dimensional medical image. The first and the second object are here arranged in an object under examination. The method comprises a method step of providing at least two exploratory views of the first and the second object. The exploratory views here map the first and the second object from different angles. The method moreover comprises a method step of segmenting the first object in the exploratory views. First two-dimensional object masks are here determined. The method comprises a further method step of segmenting the second object in the exploratory views. Second two-dimensional object masks are here determined. The method comprises a further method step of determining a first three-dimensional object mask of the first object as a function of the first two-dimensional object masks. The method moreover comprises a method step of determining a second three-dimensional object mask of the second object as a function of the second two-dimensional object masks. The method moreover comprises a method step of determining an overlap of the first and the second object for at least one capture trajectory for recording the three-dimensional medical image as a function of the first and the second three-dimensional object mask. The overlap is here determined from a projective overlap of the first and the second object in hypothetical projection captures which are obtained from the at least one capture trajectory.

The three-dimensional medical image is recorded by recording a plurality of two-dimensional projection captures of the object under examination. At least two projection captures of the object under examination are here recorded from different angles. In particular, the angles or capture angles on recording the projection captures may differ for all the projection captures. The projection captures are recorded along a capture trajectory, i.e. the angles relative to the object under examination from which the projection captures are captured are predetermined or restricted or limited by the selection of the capture trajectory. In other words, the projection captures are recorded from the standpoint of the capture trajectory. The three-dimensional medical image can then be reconstructed as a function of the plurality of projection captures. The three-dimensional medical image may in particular be recorded with a system which is configured for recording the projection captures, or an imaging system. The system or imaging system is here an imaging system, in particular a medical imaging system.

The object under examination may in particular be at least one part of a human or an animal. Alternatively, the object under examination may be at least one part of an inanimate object. The three-dimensional medical image maps the object under examination.

The first and the second object are here arranged in the object under examination. In other words, the first and the second object are arranged within the object under examination. In other words, the first and the second object are surrounded by the object under examination. The first and the second object are thus also mapped together with the object under examination in the three-dimensional medical image. In the following description, the designation of the object under examination also includes the first and second object arranged in the object under examination.

In particular, in some embodiments of the present invention, the first object may be at least approximately isotropic, i.e. at least approximately spherical. In other words, an artifact, for example a metal artifact, produced by the first object in a projection capture may be at least approximately independent of the angle or capture angle.

The first object may be configured such that it can produce or cause artifacts, in particular metal artifacts, in the projection captures.

In some embodiments of the present invention, more than one first and/or more than one second object can be arranged in the object under examination. The method described hereinafter can then be applied analogously to the plurality of first objects and the plurality of second objects.

In the method step of providing the at least two exploratory views, the at least two exploratory views are in particular provided by a system or imaging system which records the exploratory views or by a database. The exploratory views may thus be provided directly by the imaging system which records the exploratory views. Alternatively, the exploratory views may be stored or saved in a database and provided by the latter. The database may in particular be stored or saved on a cloud server or on a local server.

The exploratory views are two-dimensional projection captures of the first and second object. In other words, the exploratory views are two-dimensional projection captures of the object under examination, in which the first and the second object are arranged. The exploratory views may have a lower resolution or image quality than the projection captures for reconstructing the three-dimensional medical image. The exploratory views form the first and the second object from at least two different angles or capture angles. In particular, each exploratory view can map the object under examination or the first and the second object from another angle. In particular, the exploratory views may have been recorded with the same imaging system as that with which the three-dimensional medical image is also to be recorded.

An exploratory view comprises a plurality of pixels. The pixels are here arranged in a two-dimensional pixel matrix. A pixel value is assigned to each pixel. The pixel value of a pixel here describes a property of a region of the object under examination which is projected onto the pixel in the corresponding exploratory view. In addition, the pixel value may moreover describe a property of a region of the first and/or second object when the corresponding region of the first and/or second object is likewise projected onto the pixel. In particular, each of the exploratory views may comprise such a plurality of pixels.

Each of the objects, the first and the second object, is mapped in at least two exploratory views. The exploratory views in which the first object is mapped may here be entirely or partially identical to the exploratory views in which the second object is mapped. In other words, the first and the second object may be at least partially mapped in the same exploratory views. The exploratory views in which the first object is mapped may alternatively differ from the exploratory views in which the second object is mapped.

In the method step of segmenting the first object in the exploratory views, the first object in the exploratory views, in particular in all the exploratory views, is segmented. In particular, the first object in all the exploratory views in which it is mapped is segmented.

On segmentation, the first object may in particular be segmented by thresholding. On the basis of their pixel values, the pixels in the exploratory views may here be assigned to the first object or alternatively not assigned to the first object. In particular, those pixels whose pixel values are located in a first value range or numerical range may be assigned to the first object. All the other pixels are not assigned to the first object.

Alternatively or additionally, the first object can be segmented as described hereinafter by application of a first trained function to the exploratory views.

Alternatively or additionally, the first object in the exploratory views can be manually segmented. An expert, for example a radiologist, may for this purpose manually segment the first object in the exploratory views.

On segmentation of the first object in the exploratory views, the first two-dimensional object masks are determined. In particular, a first two-dimensional object mask can be determined for each exploratory view. A first two-dimensional object mask here comprises exactly as many pixels as the exploratory view for which the first two-dimensional object mask was determined. Each pixel of the first two-dimensional object mask thus corresponds to a pixel of the corresponding exploratory view for which the first two-dimensional object mask was determined. The pixels of the first two-dimensional object masks which have been assigned to the first object in accordance with the respectively corresponding exploratory view may here comprise a pixel value of one. All the other pixels of the first two-dimensional object mask may comprise a pixel value of zero. Alternatively, the pixels of the first two-dimensional object masks assigned to the first object may comprise a zero and all other pixels of the first two-dimensional object mask may comprise a one.

The method step of segmenting the second object may be carried out analogously to the segmentation of the first object. Segmentation may here proceed as described above by thresholding and/or by application of a second trained function to the exploratory views and/or manually for example by a radiologist. The second trained function is here configured analogously to the first trained function and adapted to segmentation of the second object. On segmentation by thresholding, the value range or numerical range of the pixel values of the pixels which are assigned to the second object may differ from the numerical range of the pixel values of the pixels which are assigned to the first object. In particular, the two numerical ranges may be disjunctive. Alternatively, the two numerical ranges at least partially overlap. The second two-dimensional object masks may here be configured analogously to the first two-dimensional object masks.

Segmentation of the first object and the second object may proceed separately or simultaneously depending on the degree of overlap of the two objects in the exploratory views. Segmentation advantageously proceeds separately as described above.

If the first and the second object are segmented simultaneously, segmented exploratory views are first of all determined in which the first and the second object are segmented together. Determination of the segmented exploratory views may here proceed as described above by way of thresholding and/or by way of applying a trained function. In the segmented exploratory views, the pixels of the segmented exploratory views are assigned either to one of the two objects or to neither of the objects. The pixel values of the pixels in the exploratory views which are assigned to none of the objects may have been replaced in the segmented exploratory views for example by a zero or a NaN value. The pixel values of the pixels which are assigned to the first or the second object are unchanged in the segmented exploratory views in comparison with the exploratory views. The pixels which are already assigned to the two objects may in each case be assigned to one of the two objects by a second segmentation. This may in particular likewise proceed by thresholding or a further trained function. On thresholding, a first value range or numerical range may be defined for the first object and a second value range or numerical range for the second object. The first and the second numerical range may here be disjunctive. Alternatively, the first and the second numerical range may overlap. The pixels having pixel values located in the first numerical range may then be assigned to the first object. Analogously, the pixels located in the second numerical range may be assigned to the second object. The first and second two-dimensional object masks configured as described above are here determined.

In the method step of determining the first three-dimensional object mask, the first three-dimensional object mask is determined as a function of the first two-dimensional object masks. The first three-dimensional object mask describes a three-dimensional extent or shape of the first object and its three-dimensional position in space.

Analogously, in the method step of determining the second three-dimensional object mask, the second three-dimensional object mask is determined as a function of the second two-dimensional object masks. The second three-dimensional object mask here describes a three-dimensional extent or shape of the second object and its three-dimensional position in space.

The first and the second three-dimensional object mask may be brought into a spatial relationship with one another. In other words, the first and the second three-dimensional object mask may serve to depict or map a spatial relationship between the first and the second object. In other words, the spatial position of the first object relative to the spatial position of the second object can be mapped or depicted by the first and the second three-dimensional object mask.

In the method step of determining the overlap of the first and the second object for at least one capture trajectory, the extent of the overlap between the first and the second object is determined for at least one capture trajectory as a function of the first and the second three-dimensional object mask. The at least one capture trajectory is here configured for recording the three-dimensional medical image. In other words, a plurality of projection captures of the object under examination including the first and the second object can be recorded along the at least one capture trajectory. The three-dimensional medical image can then be determined or reconstructed as a function of these projection captures. In particular, the at least one capture trajectory forms at least one part of a circular path or an ellipse around the object under examination.

As a function of the first and the second three-dimensional object mask, hypothetical projection captures of the first and the second object from different angles or capture angles can be simulated by a forward projection. The angles are here restricted or predetermined by the at least one capture trajectory.

The overlap is here determined from projective overlaps of the first and the second object in the hypothetical projection captures for the at least one capture trajectory. In other words, with the assistance of the spatial relationship between the first and the second object known from the first and the second three-dimensional object mask, the projective overlap can be simulated for a plurality of angles or hypothetical projection captures which can be recorded along the at least one capture trajectory. In other words, it is possible to determine the projective overlap for the hypothetical or simulated plurality of projection captures along the capture trajectory. In other words, the projections of the first and the second object can be simulated for the different hypothetical projection captures along the capture trajectory. The projective overlap for the different hypothetical projection captures can in each case be determined from the projections. The projective overlap may here for example indicate for the hypothetical projection captures by how many pixels of the hypothetical projection captures the projection of the first object overlaps with the projection of the second object. In particular, it is possible to simulate for each hypothetical projection capture how many pixels map both the first and the second object or how many pixels map an overlap of the first and the second object. The projective overlap of each hypothetical or simulated projection capture may here indicate the sum or the number of pixels which map an overlap of the two objects.

The overlap for the at least one capture trajectory may then correspond to the sum of the projective overlaps of the individual hypothetical or simulated projection captures. The sum may here be divided by the number of hypothetical projection captures simulated for the at least one capture trajectory or by the number of determined projective overlaps and thus normalized.

In particular, it is possible to determine the overlap for a plurality of capture trajectories in this manner. In each case hypothetical projection captures from the different angles may here be simulated as a function of the different capture trajectories which map or depict the overlap of the first and the second object. The angles are here restricted or limited by the respective capture trajectory.

In those embodiments in which more than one first and/or more than one second object are arranged in the object under examination, the overlap may be determined in that the overlap indicates the extent to which all the first objects overlap with all the second objects. In other words, the overlap can be determined as the overlap of the sum of the first objects with the sum of the second objects. In particular, the plurality of first objects can be handled for this purpose like a large first object and the plurality of second objects like a large second object.

The inventor has found that the dose which is not directly necessary for recording the three-dimensional medical image can be reduced to that for recording the exploratory views. The inventor has found that only a small number of (at least two) exploratory views, advantageously of low resolution, is necessary for determining the first and the second three-dimensional object mask. In this manner, a dose administered to the object under examination can be kept as low as possible if X-ray imaging is used for the exploratory views. The inventor has moreover found that, with the assistance of the described method, it is possible to determine the overlap as a function of the spatial position of the two objects. Using the described method, it is possible to determine the overlap for arbitrarily shaped objects, in particular also for isotropic objects.

According to one aspect of embodiments of the present invention, the three-dimensional medical image and the at least two exploratory views are recorded and provided by way of an X-ray system.

The three-dimensional medical image may thus in particular be a three-dimensional medical X-ray image. The three-dimensional medical image may for this purpose be recorded with the X-ray system. The X-ray system may here in particular be a C-arm system or a computed tomography (CT) system. The X-ray system may here comprise an X-ray tube for emitting X-rays and an X-ray detector for recording or receiving or detecting the X-rays. The object under examination is here arranged between the X-ray tube and the X-ray detector. The X-rays recorded with the X-ray detector may have at least in part passed through the object under examination prior to being recorded. A projection capture of the object under examination may thus be recorded with the X-ray detector. The three-dimensional medical image is recorded with the X-ray system by recording a plurality of projection captures of the object under examination. At least two projection captures of the object under examination are here recorded from different angles. In particular, the angles or capture angles on recording the projection captures may differ for all the projection captures. For this purpose, the X-ray system travels along the capture trajectory around the object under examination. At least the X-ray detector or the X-ray tube, in particular the X-ray detector and the X-ray tube, are here moved along the capture trajectory around the object under examination. The plurality of projection captures is recorded along this capture trajectory. The three-dimensional medical image can then be reconstructed as a function of the plurality of projection captures.

The exploratory views may be recorded with the X-ray system analogously to the projection captures.

The inventor has found that the method is in particular suitable for optimizing the recording of three-dimensional medical images with an X-ray system. The inventor has found that, in particular in X-ray imaging, overlaps between different objects can result in incorrect depiction or mapping in the three-dimensional medical image which may in turn lead to an erroneous diagnosis or treatment or render these impossible. In other words, the inventor has found that, in particular in X-ray imaging, object overlap is of great significance. The inventor has found that in particular the metal artifacts which occur in X-ray imaging can result in problematic overlaps between objects which prevent or at least complicate correct reconstruction of the overlapped objects in the three-dimensional medical image.

According to a further aspect of example embodiments of the present invention, a first absorption coefficient of the first object is greater than a second absorption coefficient of the second object.

In other words, the first object attenuates X-rays more strongly than the second object. The absorption coefficient of an object thus describes an attenuation of X-rays by the object and the greater an object's absorption coefficient, the more strongly are the X-rays attenuated on passing through the object. The greater an object's absorption coefficient, the greater the probability that the object will produce an artifact in the projection captures or in the three-dimensional medical image. The artifact may in particular be a metal artifact.

The inventor has found that the first object can overlap with the second object in the projection captures and/or in the three-dimensional medical image if it has a greater absorption coefficient than the second object. The inventor has found that, in particular in X-ray imaging, a greater absorption coefficient can result in "metal artifacts". In other words, an object with a large absorption coefficient in the exploratory views and/or in the projection images and/or in the three-dimensional medical image can produce or bring about or cause metal artifacts. These metal artifacts may in turn overlap with another object, in particular the second object, in such manner that, in the event of a non-optimal selection of the capture trajectory, a meaningful reconstruction of the second object as a function of the projection captures is not possible.

According to a further aspect, the capture trajectory is dependent on a positioning of the object under examination.

In other words, the angles or capture angles of the projection captures which are recorded along a capture trajectory depend on how the object under examination is positioned relative to the imaging system for recording the projection captures, in particular relative to the X-ray system. In other words, the capture trajectory can be varied either by an adapted movement of the imaging system, for example of the X-ray system, and/or by adapting the positioning of the object under examination.

This means, if a specific capture trajectory is to be traveled along or if projection captures are to be recorded along a specific capture trajectory, that either the movement of the imaging system, for example of the X-ray system, can be adapted and/or that the object under examination can be appropriately positioned relative to the imaging system, for example the X-ray system.

The capture trajectory is thus defined relative to the object under examination. In other words, the capture trajectory extends in a specific relationship to the object under examination or to the first and the second object. In other words, the capture trajectory is defined as a function of a positioning of the object under examination. In particular, a spatial position of the capture trajectory is thus dependent on the positioning of the object under examination.

The inventor has found that adapting the capture trajectory does not necessarily require adaptation of the imaging system or of the movement of the imaging system, in particular of the X-ray system, on recording the projection captures but that under certain circumstances suitable, adapted positioning of the object under examination is sufficient. The inventor has found that, under certain circumstances, adapting the positioning to the capture trajectory is easier than producing or traveling along the capture trajectory purely by an adapted movement of the imaging system. The inventor has found that, by adapting the positioning of the object under examination to the capture trajectory, it is possible to avoid having to move the imaging system in such a way that an operator or a person who is carrying out a medical intervention on the object under examination, is impeded.

According to a further aspect of example embodiments of the present invention, the method step of determining an overlap of the first and the second object is carried out for more than one capture trajectory.

In particular, hypothetical projection captures can be simulated for more than one capture trajectory as a function of the first and the second three-dimensional object masks. The capture trajectories here in each case bound the angles of the hypothetical projection captures relative to the object under examination. A projective overlap of the first and the second object can be determined as described above for each hypothetical projection capture.

As described above, an overlap or a total overlap can be determined for each capture trajectory from the corresponding hypothetical projection captures or from the corresponding projective overlaps.

As described above, the overlap can depend on the sum of the projective overlaps. The sum may here be normalized by the number of hypothetical projection captures or projective overlaps. In this manner, it is in particular also possible to enable a comparison between different capture trajectories in the event of a varying number of simulated hypothetical projection captures or projective overlaps determined therefrom.

The inventor has found that it is possible by way of the described method to compare different capture trajectories with regard to their overlap. The inventor has found that this comparison may initially be based on purely theoretical considerations without further radiation exposure or measurement time for recording projection images. The inventor has moreover found that the overlap is a suitable measure for determining the suitability of a capture trajectory which can be straightforwardly determined for the different capture trajectories as a function of the first and the second three-dimensional object mask.

According to a further aspect of example embodiments of the present invention, the method moreover comprises a method step of determining an optimum capture trajectory. The optimum capture trajectory is here that capture trajectory for which the least overlap of the first and the second object was determined. The method comprises a further method step of recording the three-dimensional medical image as a function of the optimum capture trajectory.

The previously determined overlaps of the different capture trajectories are thus compared in the method step of determining the optimum capture trajectory. On the basis of this comparison, it is possible to determine the minimum or least overlap. The capture trajectory for which this least overlap was determined is defined as the optimum capture trajectory. The projection captures which are recorded for the optimum capture trajectory thus have the least projective overlap in comparison with the projection captures of the other capture trajectories, for which the overlap was in each case determined. This means that the comparatively least overlap of the first and the second object in the projection images is expected along the optimum capture trajectory. "Comparatively" here relates to the capture trajectories taken into account or to the capture trajectories for which the overlap was determined.

The optimum capture trajectory can thus be defined as the capture trajectory for recording the three-dimensional medical image.

In the method step of recording the three-dimensional medical image, the three-dimensional medical image is recorded as a function of the optimum capture trajectory. The imaging system, in particular the X-ray system, is here appropriately actuated for recording the three-dimensional image. In other words, the imaging system for recording the three-dimensional medical image is actuated such that a plurality of projection images are recorded along the optimum capture trajectory. The imaging system, in particular the X-ray system, can be appropriately moved for this purpose. Alternatively or additionally, the positioning of the object under examination can be appropriately adapted.

The three-dimensional medical image can then be reconstructed as a function of the projection captures recorded in this manner.

The inventor has found that an optimum capture trajectory for recording the three-dimensional medical image can be determined with the described method. The inventor has moreover found that, as a function of the optimum capture trajectory determined in this manner, the imaging system, in particular the X-ray system, can be appropriately actuated for recording the three-dimensional medical image, such that a plurality of projection images of the object under examination are recorded along the optimum capture trajectory.

According to a further aspect of example embodiments of the present invention, the object under examination is positioned by way of a positioning device. Prior to recording the three-dimensional medical image, the method here moreover comprises a method step of positioning the object under examination in accordance with the optimum capture trajectory. The positioning device is here automatically actuated as a function of the optimum capture trajectory such that the object under examination is positioned in accordance with the positioning for the optimum capture trajectory.

The positioning device is configured to immobilize the object under examination in a specific position during recording of the three-dimensional medical image. In particular, the positioning device is configured to immobilize the object under examination while the optimum capture trajectory is being traveled along. In particular, it is in this manner possible to prevent movement of the object under examination from causing the actual capture trajectory to deviate from the optimum capture trajectory relative to the object under examination or necessitating adaptation of the movement of the recording imaging system to the position of the object under examination while the optimum capture trajectory is being traveled along.

The positioning device may for example be a head shell. In this case, the object under examination is a human head. The first and the second object are then arranged in the head. The head shell is configured to set a tilt and/or rotation of the head. The head shell is moreover configured to immobilize the set tilt and/or rotation of the head.

As described above, the movement of the imaging system or of the X-ray system may be adapted for the purpose of traveling along the optimum capture trajectory. Alternatively or additionally, the positioning of the object under examination relative to the imaging system or X-ray system may be adapted. In particular, the positioning of the object under examination may be adapted such that the imaging system travels along the optimum capture trajectory relative to the object under examination even without any change to the movement of the imaging system. In other words, in some embodiments of the present invention, the imaging system can travel along a fixed capture trajectory. In order to ensure that this fixed capture trajectory corresponds to the optimum capture trajectory, the object under examination may be appropriately positioned relative to the imaging system with the positioning device.

In the method step of positioning the object under examination, the positioning of the object under examination is adapted to the optimum capture trajectory. In particular, the positioning of the object under examination may here be adapted such that the imaging system or the X-ray system can continue to carry out a fixed, unchanged movement sequence in order to travel along the optimum capture trajectory. Alternatively, the movement sequence of the imaging system or the X-ray system can additionally be adapted in order to adapt the positioning. The positioning is thus adapted such that, due to the combination of the positioning with the movement of the imaging system or X-ray system, the optimum capture trajectory is traveled along.

The positioning device can be automatically actuated in order to position the object under examination or adapt the positioning. The positioning device is here actuated such that the imaging system for recording the three-dimensional medical image, in particular the X-ray system, travels along the optimum capture trajectory relative to the object under examination.

If the positioning device is for example a head shell as described above, the tilt and/or the rotation of the head can be set automatically.

Alternatively, the positioning of the object under examination can be manually adapted. Guidance may be provided for this purpose which, as a function of the specific optimum capture trajectory, guides an operator or the object under examination itself as to how the positioning should be adapted.

The inventor has found that, alternatively or additionally to actuation of the imaging system, in particular the X-ray system, knowledge of the optimum capture trajectory may also be utilized for automatically setting or adapting the positioning of the object under examination. The inventor has found that, by adapting the positioning of the object under examination, it is possible to ensure that the optimum capture trajectory for recording the three-dimensional medical image is traveled along. The inventor has found that, in particular during a medical treatment or a medical intervention on the object under examination, adaptation of the movement of the imaging system, in particular of the X-ray system, for recording the three-dimensional medical image is not possible or is at least problematic. The inventor has found that this problem can be at least partially overcome by adaptation of the positioning of the object under examination. The inventor has found that it is in this manner possible to ensure that the optimum capture trajectory is completely automatically traveled along.

According to a further aspect of example embodiments of the present invention, the three-dimensional medical image is recorded with an X-ray system in the method step of recording the three-dimensional medical image. On recording the three-dimensional medical image, the X-ray system here travels along the optimum capture trajectory.

The X-ray system is configured as described above. In order to travel along the optimum capture trajectory, at least the X-ray detector or the X-ray tube travels along the optimum capture trajectory around the object under examination. In particular, both the X-ray detector and the X-ray tube can move along the optimum capture trajectory around the object under examination. The object under examination is here arranged between the X-ray detector and the X-ray tube. When the X-ray tube and the X-ray detector move around the object under examination, the X-ray detector and the X-ray tube in particular move such that a constant distance is maintained between the X-ray tube and the X-ray detector. For example, the X-ray tube and the X-ray detector can be arranged on a C-arm. The X-ray tube and the X-ray detector are also moved by movement of the C-arm.

In particular, the movement of the X-ray tube and of the X-ray detector can be adapted to the optimum capture trajectory. In other words, movement relative to the object under examination can be adapted to the optimum capture trajectory. In the case of a C-arm, the C-arm can be rotatably mounted about a vertical axis. The C-arm can moreover be tiltably mounted about a horizontal axis. The positions of the X-ray tube and the X-ray detector can be adapted to the optimum capture trajectory by rotating and tilting the C-arm.

The inventor has found that, alternatively or additionally to positioning the object under examination, the optimum capture trajectory can be traveled along by suitable movement of the X-ray system on recording the three-dimensional medical image. In other words, the movement of the X-ray system can be adapted to the optimum capture trajectory.

According to a further aspect of example embodiments of the present invention, the method step of recording the three-dimensional medical image comprises a method step of recording a plurality of two-dimensional projection captures of the object under examination along the optimum capture trajectory. At least two projection captures are here recorded from varying angles.

The method step of recording the three-dimensional medical image moreover comprises a method step of reconstructing the three-dimensional medical image as a function of the plurality of two-dimensional projection captures. A metal artifact correction is here optionally carried out on reconstruction of the three-dimensional medical image.

In the method step of recording the plurality of two-dimensional projection captures, the two-dimensional projection captures are recorded, while the imaging system, in particular the X-ray system, is traveling along the optimum capture trajectory relative to the object under examination. In particular, a two-dimensional projection capture can be recorded at regular intervals while the optimum capture trajectory is being traveled along. The regularity of the intervals may here relate to a regularity in time and/or space.

The optimum capture trajectory may in particular form at least one part of a circular path or elliptical path around the object under examination. At least two projection captures of the plurality of captures are recorded at varying or different positions of the optimum capture trajectory. The angles or capture angles of the at least two projection captures thus differ relative to the object under examination.

In some embodiments of the present invention, a projection capture is in each case recorded at specific angular steps. In other words, a projection capture is in each case recorded at fixed angular steps along the optimum capture trajectory. If an X-ray system is used for recording the three-dimensional medical image, a projection capture is recorded whenever the X-ray detector and/or the X-ray tube have moved onward by a specific angle along the optimum capture trajectory. In particular, each projection capture may then have been recorded from a different angle relative to the object under examination.

In the method step of reconstructing the three-dimensional medical image, the three-dimensional medical image is reconstructed as a function of the plurality of previously recorded projection images. Reconstruction can be based on a known reconstruction algorithm. For example, a filtered backprojection of the plurality of two-dimensional projection captures may be carried out for reconstructing the three-dimensional medical image.

A metal artifact correction may optionally be carried out on reconstruction of the three-dimensional medical image. Metal artifact correction can be based on a known algorithm. For example, metal artifact correction can be carried out as described in Meyer, Esther, et al. "Normalized metal artifact reduction (NMAR) in computed tomography." Medical Physics 37.10 (2010): 5482-5493.

Further corrections may optionally be carried out on reconstruction of the three-dimensional medical image. For example, a noise correction can be carried out.

The inventor has found that, as is known from the corresponding imaging, it is possible to record two-dimensional projection captures along the optimum capture trajectory which are suitable for use for reconstructing the three-dimensional medical image.

According to a further aspect of example embodiments of the present invention, the method steps of segmenting the first object and segmenting the second object are based on thresholding.

Thresholding can here be configured as described above. In particular, thresholding involves grouping the pixels of the exploratory views as a function of their pixel values. In particular, a first numerical range or value range can be defined for the first object. A second numerical range or value range can be defined analogously for the second object. The first and the second numerical range may here be disjunctive. Alternatively, the first and the second numerical range may at least partially overlap or intersect. The extremes of the first and the second numerical range here in each case form the threshold values which are of relevance for segmentation of the first and the second object.

On segmentation of the first object, all the pixels whose pixel value lies within the first numerical range are assigned to the first object or grouped as belonging to the first object. All the other pixels of the exploratory captures are grouped as not belonging to the first object. A first two-dimensional object mask is here determined for each exploratory view. In particular, the first two-dimensional object masks determined on segmentation of the first object may in each case contain exactly as many pixels as the corresponding exploratory view, as a function of which they were in each case determined. Each pixel of a first two-dimensional object mask is associated with or assigned to an exploratory view pixel. The pixel values of the pixels of the first two-dimensional object masks which are in each case associated with an exploratory view pixel which is assigned to the first object can be set to one. All the other pixel values of the first two-dimensional object mask can be set to zero. Alternatively, the pixel values of the pixels of the first two-dimensional object masks which are associated with an exploratory view pixel which is assigned to the first object can be set to zero. All the other pixel values of the first two-dimensional object masks can then be set to one.

Segmentation of the second object may proceed analogously to segmentation of the first object, wherein the second two-dimensional object masks are determined. Segmentation here proceeds as a function of the second numerical range or value range.

The inventor has found that one simple form of segmentation is based on thresholding. The inventor has found that the first and the second object can in particular be effectively segmented by way of thresholding if they do not excessively overlap in the exploratory captures.

According to a further aspect of example embodiments of the present invention, the method step of segmenting the first object comprises a method step of applying a first trained function to the exploratory views. The first two-dimensional object masks are here determined. Alternatively or additionally, the method step of segmenting the second object comprises a method step of applying a second trained function. The second two-dimensional object masks are here determined.

In general, a trained function mimics cognitive functions which people associate with human thinking. In particular, training based on training data can adapt the trained function to new circumstances and recognize and extrapolate patterns.

In general, parameters of a trained function can be adapted by way of training. In particular, supervised training, semi-supervised training, unsupervised training, reinforcement learning and/or active learning can be used for this purpose. Representation learning, which is alternatively known as feature learning, can furthermore be used. In particular, the parameters of the trained functions can be iteratively adapted by a plurality of training steps.

In particular, a trained function can comprise a neural network, a support vector machine, a random tree or a decision tree and/or a Bayesian network and/or the trained function can be based on k-means clustering, Q-learning, genetic algorithms and/or association rules. In particular, a trained function can comprise a combination of a plurality of uncorrelated decision trees or an ensemble of decision trees (random forest). In particular, the trained function can be determined by way of XGBoosting (eXtreme Gradient Boosting). In particular, a neural network can be a deep neural network, a convolutional neural network or a convolutional deep neural network. A neural network can furthermore be an adversarial network, a deep adversarial network and/or a generative adversarial network. In particular, a neural network can be a recurrent neural network. In particular, a recurrent neural network can be a network with a long short-term memory (LSTM), in particular a gated recurrent unit (GRU). In particular, a trained function can comprise a combination of the described approaches. In particular, the approaches described here for a trained function are denoted the network architecture of the trained function.

The first trained function is configured to be applied to the exploratory views and segment the first object in the exploratory views. The first trained function can be trained for a specific shape of the first object. The first trained function can then correctly segment the first object even if the first object is for example mapped in the exploratory views not in its entirety or only in part and/or in overlapped and/or distorted manner due to overlap or artifacts. In other words, the first trained function may be configured to segment an actual shape of the first object even if the first object is mapped in the exploratory views only in part and/or is at least in part overlapped and/or distorted etc. by another object or an artifact. The first trained function can thus be configured to correct the mappings of the first object in the exploratory views where necessary. In other words, the first trained function can be configured to correct the shape of the first object in the exploratory views on segmentation if said shape is not correctly mapped. The first trained function then outputs the first two-dimensional object masks. The first two-dimensional object masks can here be configured as described above. In particular, an exploratory view can be assigned to or associated with each first two-dimensional object mask. The first two-dimensional object masks here comprise exactly as many pixels as the exploratory views associated therewith. There is thus also a one-to-one correspondence or association between in each case one pixel of the first two-dimensional object masks and one pixel of the correspondingly associated exploratory view. The pixels of the first two-dimensional object masks which are segmented with the first trained function as belonging to the first object are assigned a pixel value of one. All the other pixels are assigned a pixel value of zero. Alternatively, zero and one can be swapped.

The second trained function can be defined in relation to the second object analogously to the first trained function. By application of the second trained function to the exploratory views, it is possible to determine the second two-dimensional object masks analogously to the first two-dimensional object masks.

The inventor has found that, by application of the first and/or second trained function, it is possible to segment the first and/or the second object even if the first and the second object overlap in the exploratory views. In particular, the second object can, for example, be segmented even if it is partially overlapped in the exploratory views by the second object or by an artifact, for example a metal artifact, caused by the second object. The inventor has found that the first and/or second trained function can generally be trained to segment any desired objects. The inventor has, however, also found that the first and/or second trained functions can be trained such that they are configured to segment specific objects, in particular objects with a specific shape. First and/or second two-dimensional object masks corrected for the overlap can thus be determined.

According to a further aspect of example embodiments of the present invention, on determination of the first three-dimensional object mask, the first three-dimensional object mask is determined by way of an unweighted backprojection of the first two-dimensional object masks. Alternatively or additionally, on determination of the second three-dimensional object mask, the second three-dimensional object mask is determined by way of an unweighted backprojection of the second two-dimensional object masks.

Unweighted backprojection of the first and/or the second two-dimensional object mask may, as is known from the prior art, be determined, in which case the more two-dimensional object masks are available for the backprojection, the more accurately is it possible to determine the corresponding three-dimensional object mask. In particular, two two-dimensional object masks of an object are sufficient in order to determine a three-dimensional object mask of the object or at least an approximation of such a mask by way of an unweighted backprojection.

The inventor has found that the first and/or second three-dimensional object mask can be determined by way of unweighted backprojection as a function of the first or second two-dimensional object masks even if only a few, i.e. at least two, two-dimensional first or second object masks are available for the unweighted backprojection. The inventor has found that unweighted backprojection is suitable for determining or at least estimating the first and/or second three-dimensional object mask as a function of the first or second two-dimensional object masks.

According to a further aspect of example embodiments of the present invention, the first three-dimensional object mask is determined in the method step of determining the first three-dimensional object mask by way of segmentation, in particular thresholding, of the backprojected first two-dimensional object masks. Alternatively or additionally, the second three-dimensional object mask is determined in the method step of determining the second three-dimensional object mask by way of segmentation, in particular by way of thresholding, the backprojected second two-dimensional object masks.

Backprojection of the first and/or second two-dimensional object masks involves a plurality of voxels which are arranged in a three-dimensional voxel matrix. A voxel value which describes an intensity is assigned to each of the voxels.

On segmenting by way of thresholding, the region with the greatest voxel values, in particular in the backprojection of the first and/or second two-dimensional object masks, can be segmented. Alternatively, the region with the smallest voxel values can be segmented. The segmented region can correspond to the first or second three-dimensional object mask. In particular, a threshold value can be defined for thresholding. All the voxels having voxel values greater than the threshold value can then be assigned to the first and/or the second three-dimensional object mask. Alternatively, all the voxels having voxel values smaller than the threshold value can then be assigned to the first and/or second three-dimensional object mask.

Alternatively, segmentation for determining the first three-dimensional object mask can proceed by application of a third trained function. Alternatively, segmentation for determining the second three-dimensional object mask can proceed by application of a fourth trained function. The third and/or the fourth trained function may here be configured as described above in general for trained functions. The third and/or the fourth trained function may in general be configured for segmenting three-dimensional object masks for objects having any desired shape. Alternatively, the third trained function can be configured to segment a three-dimensional object mask of the first object. The third trained function is here trained for the specific shape of the first object. The fourth trained function can analogously be trained specifically for segmenting a three-dimensional object mask of the second object. The fourth trained function can here be trained specifically to segment a three-dimensional object mask of an object with the shape of the second object. As in the case of segmentation of the first and/or second object by application of the first or second trained function respectively, the first and/or second three-dimensional object mask can also be corrected with regard to its spatial extent or shape on segmentation by the third or fourth trained function respectively. In other words, on segmentation by application of the third and/or fourth trained function, prior knowledge about the shape of the first or second object can be utilized to ensure that the first or second three-dimensional object mask maps the corresponding shape.

The inventor has found that errors in the first and/or second three-dimensional object mask which arise due to unweighted backprojection can be corrected by segmentation. The inventor has found that this is in particular of relevance when only a few, in particular only two, first or second two-dimensional object masks are available for unweighted backprojection of the first and/or second two-dimensional object masks. The inventor has found that smudging in the backprojections which arises due to the small number of first or second two-dimensional object masks can be removed in this manner.

According to a further aspect of example embodiments of the present invention, the first object is a coil package. The second object is alternatively or additionally a stent.

The coil package is here configured to treat an aneurysm. In particular, the coil package can be configured for treating an aneurysm in a human head. The object under examination is in this case thus a human head. The coil package may here be of approximately isotropic configuration. The coil package may here comprise a plurality of platinum coils. The coil package is thus in particular made from a metal. The coil package can thus bring about metal artifacts in the two- or three-dimensional imaging of the coil package.

The stent may to this end be configured to widen a vessel. The stent is in particular configured to be introduced into a vessel and dilated therein. The stent may in particular be made at least in part from a metal. The stent may in particular be made at least in part from a medical special steel or from a cobalt-chromium alloy or from a cobalt-nickel alloy.

Alternatively, the second object may for example be a bleed, a dilatation, an aneurysm, a blood clot, a rupture, a fissure etc.

The inventor has found that the method for defining a capture trajectory is suitable for medical use, in particular in a human head.

According to a further aspect of example embodiments of the present invention, precisely two exploratory views are provided.

The two exploratory views here map the object under examination, comprising the first and the second object, from two varying angles relative to the object under examination.

The inventor has found that a minimum of precisely two exploratory views is necessary in order to determine, as a function of the two-dimensional exploratory views, a three-dimensional object mask of an object mapped in the exploratory views. The inventor has found that for this purpose the two exploratory views must map the object of which the three-dimensional object mask is to be determined from two different angles or capture angles or directions. The inventor has found that, by providing just two exploratory views, the dose which is administered when using an X-ray system for recording the exploratory views is minimal.

According to a further aspect of example embodiments of the present invention, the angle between the two exploratory views is between 45° and 135°. In particular, the angle between the two exploratory views is 90°.

In particular, precisely two exploratory views are provided.

In other words, the two exploratory views enclose an angle of between 45° and 135°, in particular 90°. In other words, the mapping of the object under examination of the one exploratory view has been captured or recorded from a direction of view offset by between 45° and 135°, in particular by 90°, in comparison with the other exploratory view.

The inventor has found that the angle between the two exploratory views should be sufficiently large, namely greater than 45°, in order to be able to determine a three-dimensional object mask from one of the mapped objects. The inventor has moreover found that an angle of 180° has the same effect as an angle of 0°. For this reason, the angle between the two exploratory views must also be sufficiently small, in particular less than 135°, for it to be possible to determine the three-dimensional object mask. The inventor has found that an angle of 90° between the two exploratory captures is advantageous since in this case the two "directions of view" of the two exploratory views onto the object under examination are perpendicular to one another. The two exploratory views thus together form a maximally large field of view onto the object under examination and thus onto the first and the second object.

One or more example embodiments of the present invention moreover relate to a computer-implemented training method for providing a first trained function. The training method comprises a method step of receiving first input data, wherein the first input data comprises a plurality of exploratory views of a first object. The training method moreover comprises a method step of receiving first output data, wherein the first output data comprises first two-dimensional object masks. The input data and the output data are here related to one another. The training method moreover comprises a method step of training a first function on the basis of the first input data and the first output data. The training method moreover comprises a method step of providing the first trained function.

The exploratory views which the first input data comprises are here configured as described above. In particular, each exploratory view is a two-dimensional projection capture of an object under examination. The first and the second object are here arranged in the object under examination.

The first two-dimensional object masks which the first output data comprises are configured as described above. Each object mask is here assigned to or associated with an exploratory view of the first input data. The first object from the correspondingly associated exploratory views is segmented in the first two-dimensional object masks.

In some embodiments of the present invention, the first object may have been manually segmented in at least some of the exploratory views which the first input data comprises. In particular, an expert, for example a radiologist, may have manually segmented the first object in the exploratory views. Expert knowledge, for example with regard to the shape of the first object, can be taken into account here.

In some embodiments, the first object may alternatively or additionally be segmented by way of thresholding in at least some of the exploratory views which the first input data comprises in order to determine the first two-dimensional object masks which the first output data comprises. Thresholding can here be configured as described above.

The first input data and the first output data may here be provided by a database. The database may here be a local database or a database in a cloud (storage) system.

In the method step of training the first trained function, the first function is applied to the first input data. First ascertained output data is here determined. This first ascertained output data is compared with the first output data. On the basis of this comparison, at least one parameter of the first function is adapted such that, on renewed application of the first adapted function to the first input data, the newly ascertained first output data is a better match for the first output data. This step is repeated iteratively until at least one termination criterion is met. The termination criterion may for example be a maximum number of iterations. Alternatively or additionally, the termination criterion may be undershooting of a maximum deviation between the first ascertained output data of the final iteration and the provided first output data.

In the method step of providing the first trained function, the first trained function is provided for further use, in particular for application in the above-described method.

The inventor has found that the first trained function can be trained to segment the first object even if it is partially overlapped by another object or by an artifact. The first trained function can for this purpose be trained for the shape or the three-dimensional extent of the first object. In other words, the first trained function can be trained to segment an object with the shape of the first object in the exploratory captures.

One or more example embodiments of the present invention moreover relate to a computer-implemented training method for providing a second trained function. The method comprises a method step of receiving second input data, wherein the second input data comprises a plurality of exploratory views of a second object. The method moreover comprises a method step of receiving second output data, wherein the second output data comprises second two-dimensional object masks. The second input data and the second output data are here related to one another. The method moreover comprises a method step of training a second function on the basis of the second input data and the second output data. The method moreover comprises a method step of providing the second trained function.

The description with regard to the computer-implemented training method for providing a first trained function can be applied, in relation to the second object, analogously to the computer-implemented training method for providing a second trained function. The parts of the description which relate above to the first object can be applied, in connection with training the second trained function, analogously to the second object.

The inventor has found that the advantages of the first trained function in relation to the first object can be applied analogously to the second trained function in relation to the second object.

One or more example embodiments of the present invention moreover relate to a determination system for defining a capture trajectory for recording a first and a second object in a three-dimensional medical image. The first and the second object are here arranged in an object under examination. The determination system here comprises an interface and a computing unit. The interface is here configured to record at least two exploratory views of the first and the second object. The exploratory views here map the first and the second object from different angles. The computing unit is here configured to segment the first object in the exploratory views. First two-dimensional object masks are here determined. The computing unit is here moreover configured to segment the second object in the exploratory views. Second two-dimensional object masks are here determined. The computing unit is here moreover configured to determine a first three-dimensional object mask of the first object as a function of the first two-dimensional object masks. The computing unit is here moreover configured to determine a second three-dimensional object mask of the second object as a function of the second two-dimensional object masks. The computing unit is here configured to determine an overlap of the first and the second object for at least one capture trajectory for recording the three-dimensional medical image as a function of the first and the second three-dimensional object mask. The overlap is here determined from projective overlaps of the first and the second object in hypothetical projection captures which are obtained from the at least one capture trajectory.

Such a determination system can in particular be configured to carry out the previously described method for defining a capture trajectory for recording a first and a second object in a three-dimensional medical image, and the aspects thereof. The determination system is configured to carry out this method and the aspects thereof by the interface and the computing unit being configured to carry out the corresponding method steps.

One or more example embodiments of the present invention moreover optionally relate to a first training system for providing a first trained function. The first training system comprises a first training interface and a first training computing unit. The first training interface is configured to receive first input data. The first input data here comprises a plurality of exploratory views of a first object. The first training interface is moreover configured to receive first output data. The first output data here comprises first two-dimensional object masks. The first input data and the first output data are here related to one another. The first training computing unit is configured to train a first function on the basis of the first input data and the first output data. The first training interface is moreover configured to provide the first trained function.

Such a first training system can in particular be configured to carry out the previously described method for providing a first trained function and the aspects thereof. The first training system is configured to carry out this method and the aspects thereof by the first training interface and the first training computing unit being configured to carry out the corresponding method steps.

One or more example embodiments of the present invention moreover optionally relate to a second training system for providing a second trained function. The second training system comprises a second training interface and a second training computing unit. The second training interface is configured to receive second input data. The second input data here comprises a plurality of exploratory views of a second object. The second training interface is moreover configured to receive second output data. The second output data here comprises second two-dimensional object masks. The second input data and the second output data are here related to one another. The second training computing unit is configured to train a second function on the basis of the second input data and the second output data. The second training interface is moreover configured to provide the second trained function.

Such a second training system can in particular be configured to carry out the previously described method for providing a second trained function and the aspects thereof. The second training system is configured to carry out this method and the aspects thereof by the second training interface and the second training computing unit being configured to carry out the corresponding method steps.

One or more example embodiments of the present invention also relate to a computer program product with a computer program and to a computer-readable medium. A largely software-based embodiment has the advantage that coordination systems which are already in service can also straightforwardly be retrofitted to operate in the described manner by way of a software update. In addition to the computer program, such a computer program product can optionally comprise additional elements such as for example documentation and/or additional components, as well as hardware components, such as for example hardware keys (dongles etc.) for using the software.

In particular, one or more example embodiments of the present invention also relate to a computer program product with a computer program which is directly loadable into a memory of a determination system and has program parts for carrying out all the steps of the above-described method for defining a capture trajectory for recording a first and a second object in a three-dimensional medical image, and the aspects thereof, when the program parts are run by the determination system.

In particular, one or more example embodiments of the present invention relate to a computer-readable storage medium on which program parts readable and runnable by a determination system are stored in order to carry out all the steps of the above-described method for defining a capture trajectory for recording a first and a second object in a three-dimensional medical image, and the aspects thereof, when the program parts are run by the determination system.

One or more example embodiments of the present invention also relate to a training computer program product with a training computer program and to a computer-readable training medium. A largely software-based embodiment has the advantage that first and/or second training systems which are already in service can also straightforwardly be retrofitted to operate in the described manner by way of a software update. In addition to the training computer program, such a training computer program product may comprise additional elements such as for example documentation and/or additional components including hardware components, such as for example hardware keys (dongles etc.) for using the software.

In particular, one or more example embodiments of the present invention also relate to a training computer program product with a training computer program which is directly loadable into a memory of a first and/or a second training system having program parts for carrying out all the steps of the above-described method for providing a first and/or second trained function, and the aspects thereof, when the program parts are run by the first and/or second training system.

In particular, one or more example embodiments of the present invention also relate to a computer-readable training storage medium on which program parts readable and runnable by a first and/or second training system are stored in order to carry out all the steps of the above-described method for providing a first and/or second trained function, and the aspects thereof, when the program parts are run by the first and/or second training system.

BRIEF DESCRIPTION OF THE DRAWINGS

The above-described properties, features and advantages of the present invention will become clearer and more readily comprehensible in connection with the following figures and the descriptions thereof. The figures and descriptions are not intended in any way to limit the present invention and the embodiments thereof.

Identical components in different figures are provided with corresponding reference signs. The figures are not in general true to scale.

In the figures:

Figure 1:
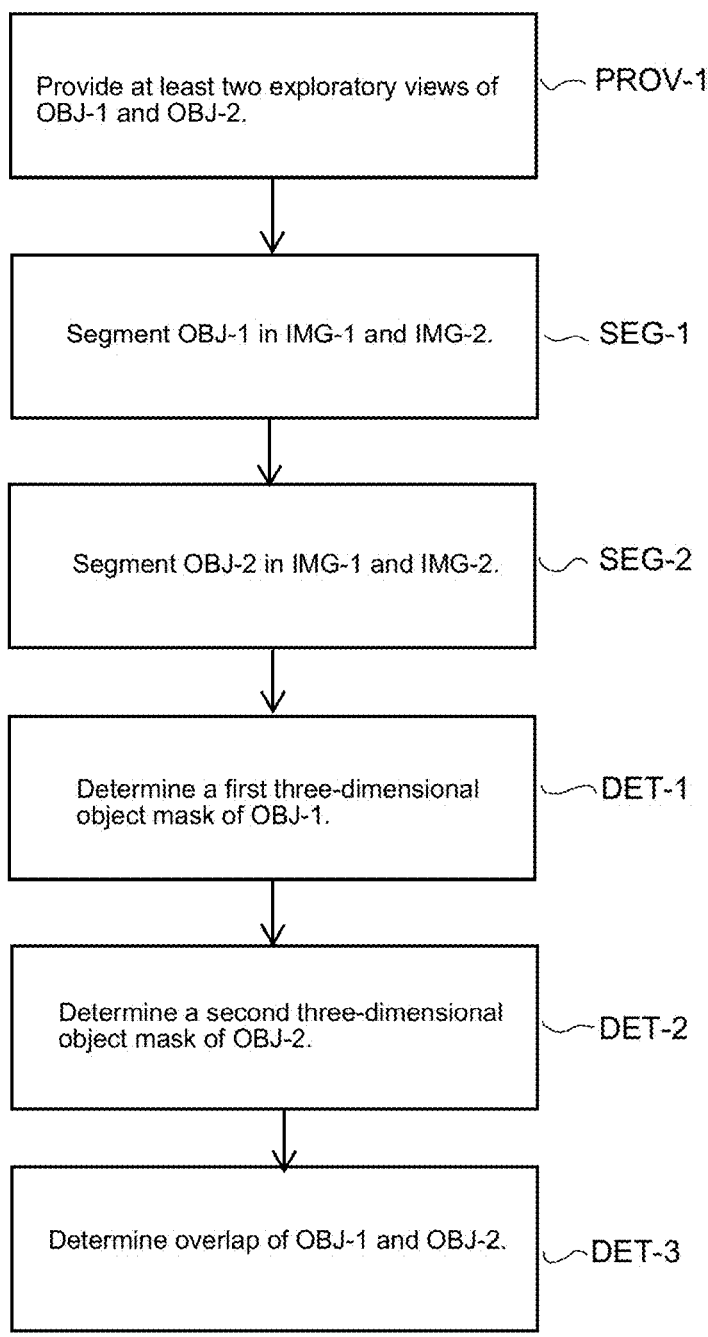
Figure 2:
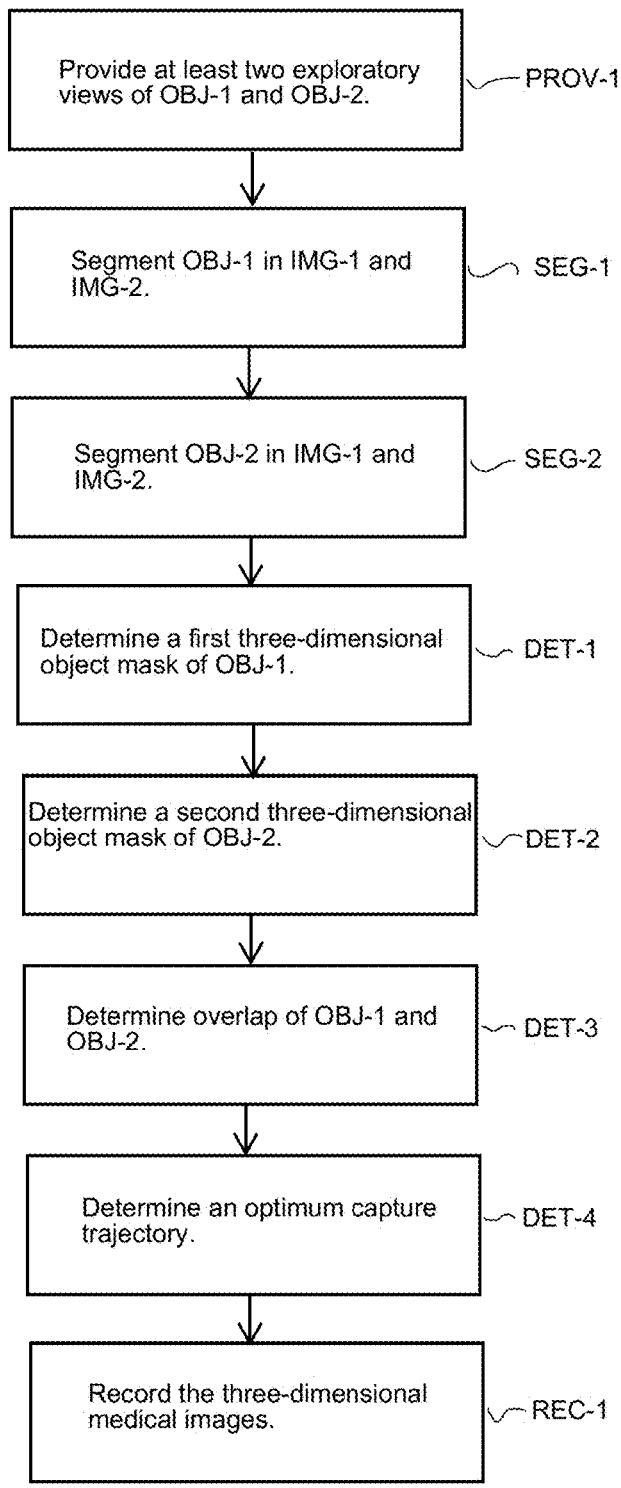
Figure 3:
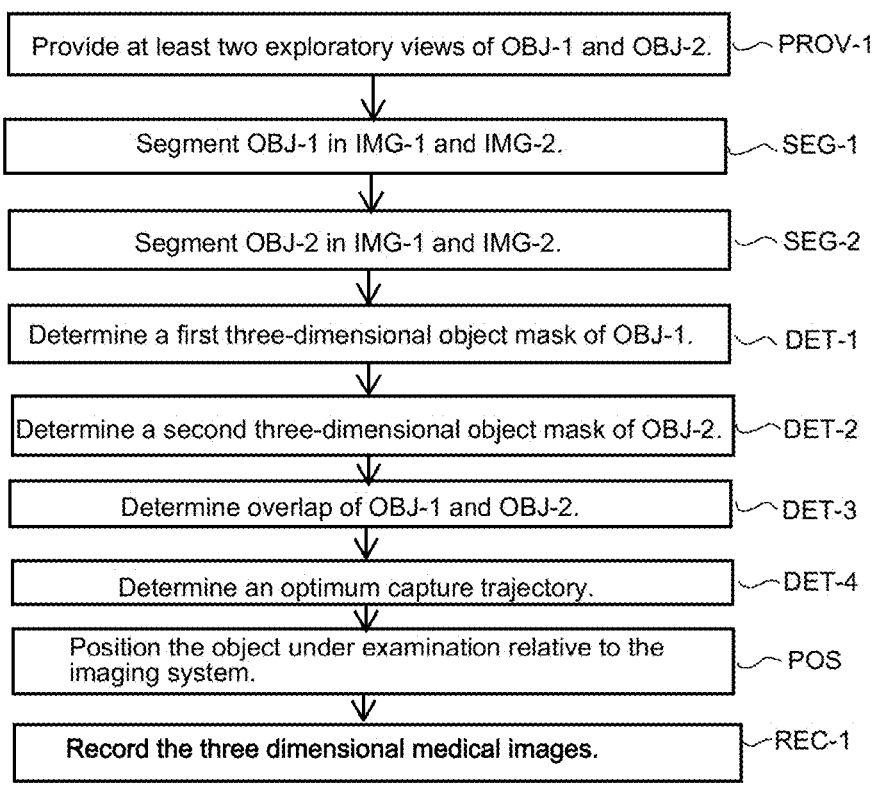
Figure 4:
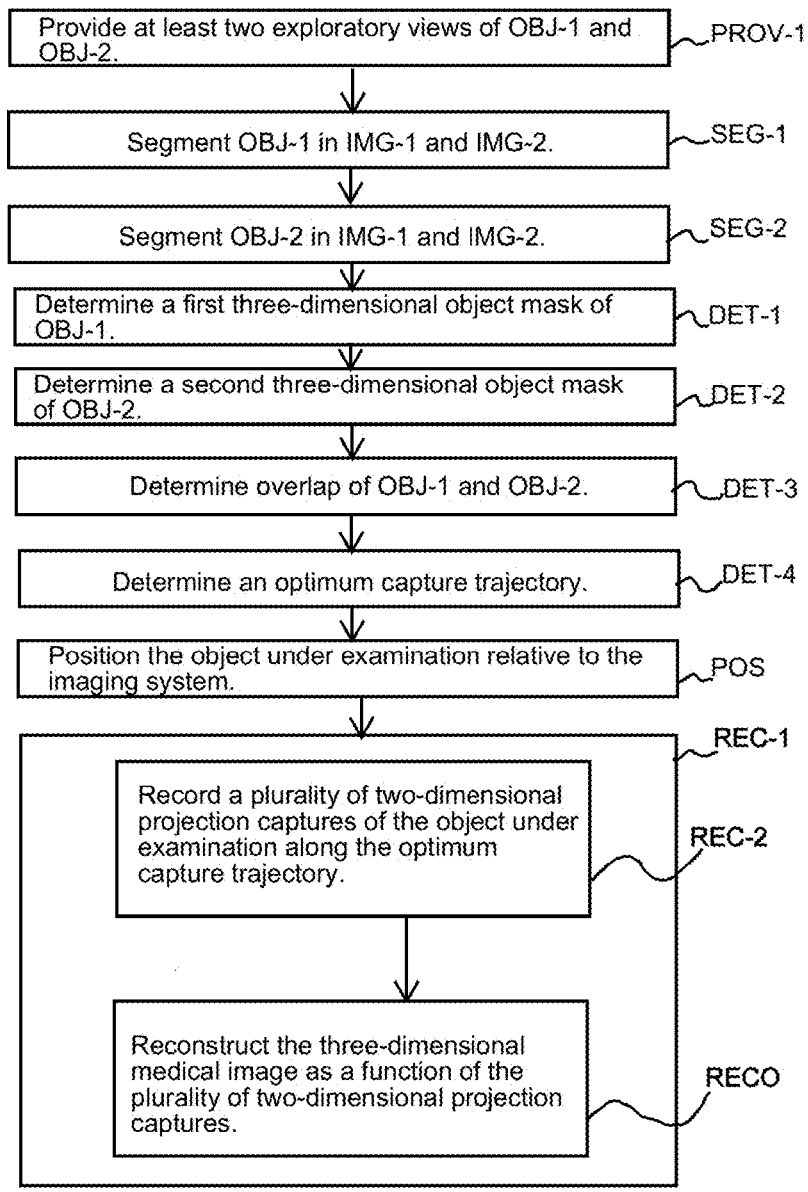
Figure 5:
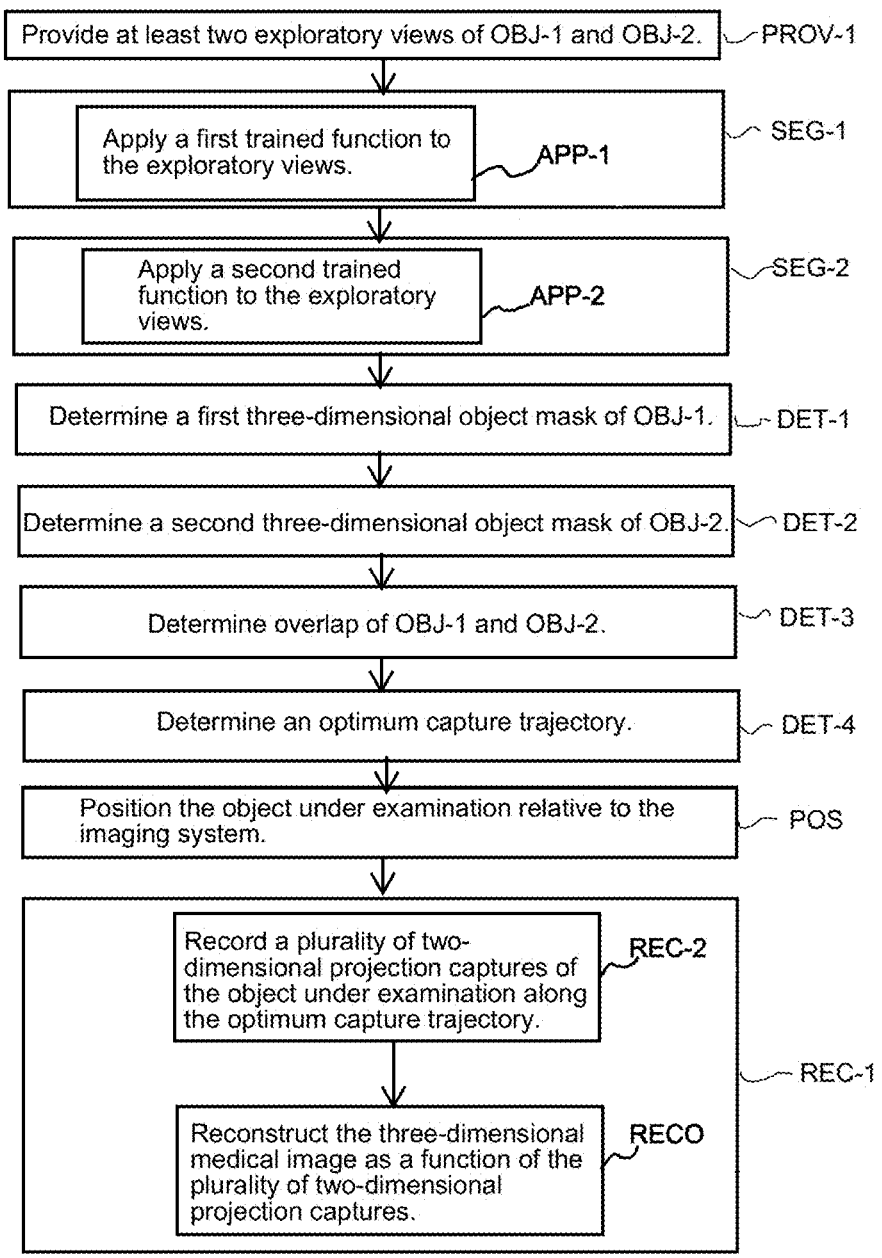
Figure 6:
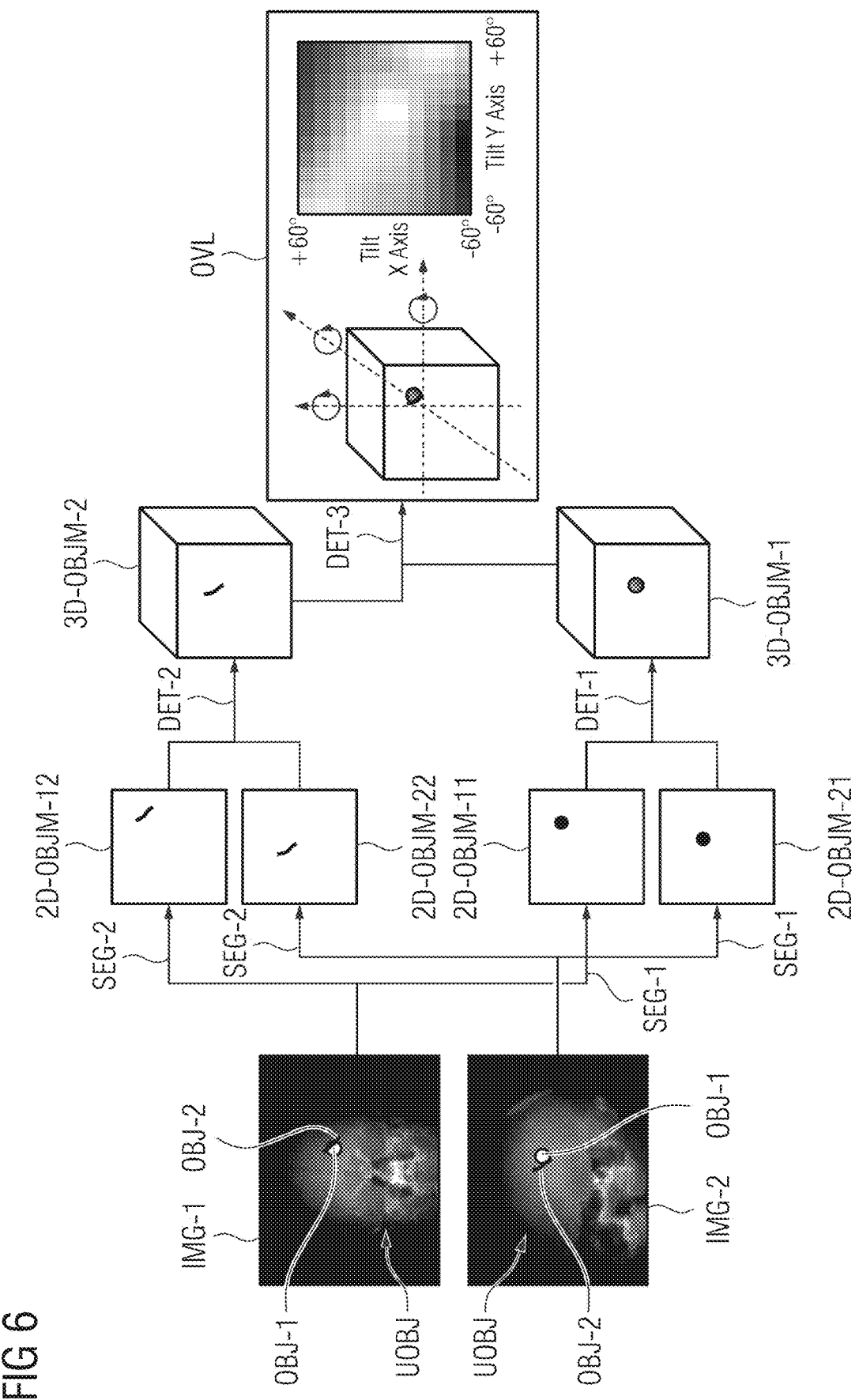
Figure 7:
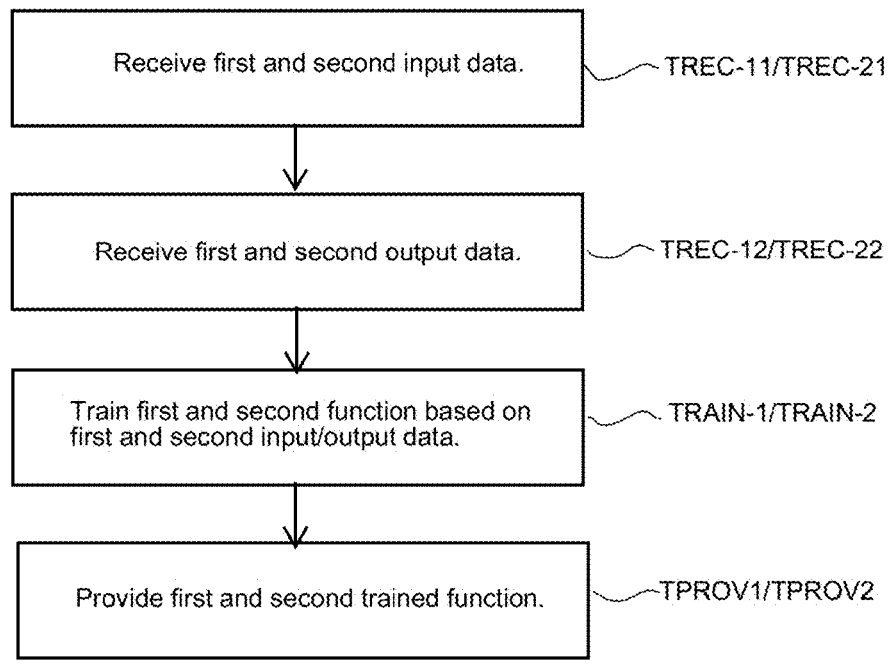
Figure 8:
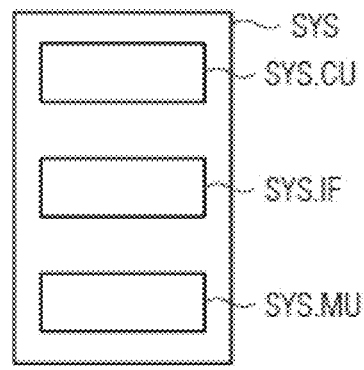
Figure 9:
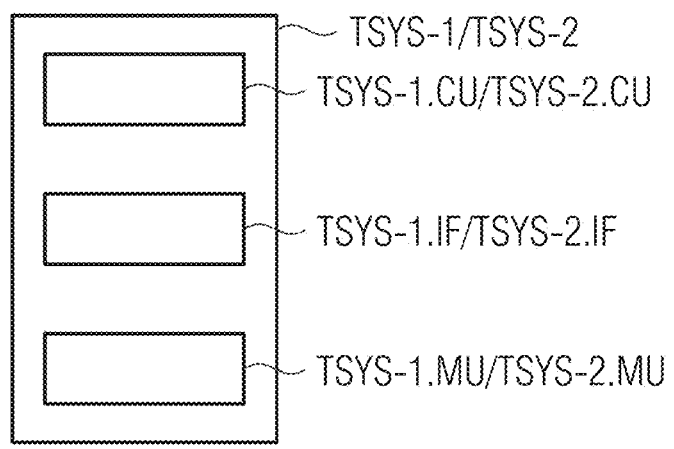

FIG. 1 shows a first exemplary embodiment of a computer-implemented method for defining a capture trajectory for recording a first and a second object in a three-dimensional medical image, FIG. 2 shows a second exemplary embodiment of a computer-implemented method for defining a capture trajectory for recording a first and a second object in a three-dimensional medical image, FIG. 3 shows a third exemplary embodiment of a computer-implemented method for defining a capture trajectory for recording a first and a second object in a three-dimensional medical image, FIG. 4 shows a fourth exemplary embodiment of a computer-implemented method for defining a capture trajectory for recording a first and a second object in a three-dimensional medical image, FIG. 5 shows a fifth exemplary embodiment of a computer-implemented method for defining a capture trajectory for recording a first and a second object in a three-dimensional medical image, FIG. 6 shows a schematic representation of a data stream on performance of the first exemplary embodiment of a computer-implemented method for defining a capture trajectory for recording a first and a second object in a three-dimensional medical image, FIG. 7 shows an exemplary embodiment of a computer-implemented training method for providing a first and/or second trained function, FIG. 8 shows a determination system for defining a capture trajectory for recording a first and a second object in a three-dimensional medical image, FIG. 9 shows a first or second training system for providing a first and/or second trained function.

DETAILED DESCRIPTION

FIG. 1 shows a first exemplary embodiment of a computer-implemented method for defining a capture trajectory for recording a first and a second object OBJ-1, OBJ-2 in a three-dimensional medical image.

The first and the second object OBJ-1 and OBJ-2 are here arranged in the object under examination UOBJ. In other words, the first and the second object OBJ-1, OBJ-2 are arranged within the object under examination UOBJ. When the phrase "object under examination" UOBJ is used hereinafter, it also includes the first and the second object OBJ-1, OBJ-2, since the latter are in a fixed spatial relationship with the object under examination UOBJ and are surrounded by the object under examination. The first and the second object OBJ-1, OBJ-2 cannot be moved independently of the object under examination UOBJ.

In some embodiments of the present invention, a first absorption coefficient of the first object OBJ-1 may be greater than a second absorption coefficient of the second object OBJ-2. In other words, at comparable extent or thickness, the first object OBJ-1 can attenuate or absorb radiation, in particular X-rays, more strongly than the second object OBJ-2.

The object under examination UOBJ may in particular be at least one part of a human or an animal. Alternatively, the object under examination UOBJ may be at least one part of an inanimate object.

The object under examination UOBJ may in particular be a human head. The first object OBJ-1 may then, for example, be a coil package which is configured for treating an aneurysm. The second object OBJ-2 may then, for example, be a stent which can be dilated in a vessel, in particular a blood vessel. Alternatively, the second object OBJ-2 may, for example, be a bleed or a mass etc.

The three-dimensional medical image can be recorded with an imaging system or system, in particular a medical imaging system. The imaging system can here be configured to record a plurality of projection captures of the object under examination UOBJ along the capture trajectory. In particular, the projection captures at least partially map the object under examination UOBJ including the first and the second object OBJ-1, OBJ-2. The projection captures can here map the object under examination UOBJ from at least two different angles or capture angles or viewing angles. In particular, each projection capture can map the object under examination UOBJ from a different angle.

The imaging system may in particular be an X-ray system. In other words, the three-dimensional medical image can in particular be recorded with an X-ray system. The X-ray system may here be a C-arm system or a computed tomography (CT) system. The X-ray system here comprises an X-ray source for emitting X-rays and an X-ray detector which is configured to detect the X-rays. The object under examination UOBJ is here arranged between the X-ray source and the X-ray detector. At least the X-ray source or the X-ray detector, in particular the X-ray source and the X-ray detector, can travel along the capture trajectory around the object under examination UOBJ. Projection captures of the object under examination UOBJ can be continuously recorded while the capture trajectory is traveled along. The three-dimensional medical image can then be reconstructed on the basis of the projection captures.

The capture trajectory may in particular form at least one part of a circular path around the object under examination UOBJ. Alternatively, the capture trajectory may form at least one part of an elliptical path around the object under examination.

In a method step of providing PROV-1 at least two exploratory views IMG-1, IMG-2, at least two exploratory views IMG-1, IMG-2 of the first and the second object OBJ-1, OBJ-2 are provided. The exploratory views IMG-1, IMG-2 map the first and the second object OBJ-1, OBJ-2 from different angles. In particular, the exploratory views IMG-1, IMG-2 map the object under examination UOBJ from two different angles.

The exploratory views IMG-1, IMG-2 are projection views of the first and the second object OBJ-1, OBJ-2. A resolution of the exploratory views IMG-1, IMG-2 may here be lower than that of the projection captures for reconstructing the three-dimensional medical image. The exploratory views IMG-1, IMG-2 can be recorded with the same imaging system with which the projection captures for reconstructing the three-dimensional medical image are to be recorded. The exploratory views IMG-1, IMG-2 may in particular likewise be recorded with the X-ray system.

Each of the exploratory views IMG-1, IMG-2 may comprise a plurality of pixels. The pixels of each exploratory view IMG-1, IMG-2 are here arranged in a two-dimensional pixel matrix. A pixel value is assigned to each pixel. The pixel value here describes at least one property of the region of the object under examination UOBJ or of the first or second object OBJ-1, OBJ-2 which is projected onto the corresponding pixel.

On provision of the at least two exploratory views IMG-1, IMG-2, the exploratory views IMG-1, IMG-2 may in particular be provided directly by the recording system, in particular by the X-ray system. Alternatively, the at least two exploratory views IMG-1, IMG-2 can be provided by a database in which the exploratory views IMG-1, IMG-2 are saved. The database may here in particular be a local database. Alternatively, the database can be saved in a cloud storage system or cloud server. The database may for example be a picture archive and communication system (PACS).

In a method step of segmenting SEG-1 the first object OBJ-1, the first object OBJ-1 in the exploratory views IMG-1, IMG-2 is segmented. First two-dimensional object masks 2D-OBJM-11, 2D-OBJM-21 are here generated or determined. In particular, a first two-dimensional object mask 2D-OBJM-11, 2D-OBJM-21 can be determined for each of the exploratory views IMG-1, IMG-2. An exploratory view IMG-1, IMG-2 is thus assigned to each first two-dimensional object mask 2D-OBJM-11, 2D-OBJM-21. A first two-dimensional object mask 2D-OBJM-11, 2D-OBJM-21 here comprises exactly as many pixels as the assigned exploratory view IMG-1, IMG-2. One pixel of the assigned exploratory view IMG-1, IMG-2 is thus assigned to each of the pixels of the first two-dimensional object masks 2D-OBJM-11, 2D-OBJM-21. On segmentation SEG-1 of the first object OBJ-1, the pixels which map the first object OBJ-1 in the exploratory views IMG-1, IMG-2 are determined. The pixels in the first two-dimensional object masks 2D-OBJM-11, 2D-OBJM-21 which correspond to these pixels are assigned a pixel value of one. All the other pixels of the first two-dimensional object masks 2D-OBJM-11, 2D-OBJM-21 are assigned a pixel value of zero. In alternative embodiments of the present invention, the assignment of zero and one can be swapped.

In a method step of segmenting SEG-2 the second object OBJ-2, the second object OBJ-2 in the exploratory views IMG-1, IMG-2 is segmented. The second object OBJ-2 is here segmented analogously as described above for the first object OBJ-1. Second two-dimensional object masks 2D-OBJM-12, 2D-OBJM-22 are here determined. The second two-dimensional object masks 2D-OBJM-12, 2D-OBJM-22 are configured analogously to the first two-dimensional object masks 2D-OBJM-11, 2D-OBJM-21. In particular, an exploratory view can in particular likewise be assigned to each second two-dimensional object mask 2D-OBJM-12, 2D-OBJM-22.

In a method step of determining DET-1 a first three-dimensional object mask 3D-OBJM-1 of the first object OBJ-1, the first three-dimensional object mask 3D-OBJM-1 of the first object OBJ-1 is determined as a function of the first two-dimensional object masks 2D-OBJM-11, 2D-OBJM-21. The first three-dimensional object mask 3D-OBJM-1 here describes a spatial extent or shape of the first object OBJ-1. In particular, the first three-dimensional object mask 3D-OBJM-1 of the first object OBJ-1 describes the spatial extent of the first object OBJ-1 in a field of view mapped in the exploratory views IMG-1, IMG-2. In particular, the first three-dimensional object mask 3D-OBJM-1 may here comprise a plurality of voxels which are arranged in a three-dimensional voxel matrix. A voxel value is here assigned to each voxel. A voxel value of one can be assigned to the voxels which map the first object OBJ-1. All the other voxels can be assigned a voxel value of zero. In alternative embodiments of the present invention, the assignment of the values zero and one can be swapped.

In a method step of determining DET-2 a second three-dimensional object mask 3D-OBJM-2 of the second object OBJ-2, the second three-dimensional object mask 3D-OBJM-2 is determined as a function of the second two-dimensional object masks 2D-OBJM-12, 2D-OBJM-22. The second three-dimensional object mask 3D-OBJM-2 is here determined analogously to the first three-dimensional object mask 3D-OBJM-1. In other words, the same relationship applies between the second three-dimensional object mask 3D-OBJM-2 and the second object OBJ-2 and the second two-dimensional object masks 2D-OBJM-12, 2D-OBJM-22 as applies between the first three-dimensional object mask 3D-OBJM-1 and the first object OBJ-1 and the first two-dimensional object masks 2D-OBJM-11, 2D-OBJM-21.

In a method step of determining DET-3 an overlap OVL of the first and the second object OBJ-1, OBJ-2, the overlap OVL of the two objects OBJ-1, OBJ-2 is determined for at least one capture trajectory. The overlap OVL is here determined as a function of the first and the second three-dimensional object mask 3D-OBJM-1, 3D-OBJM-2. The overlap OVL is here determined from projective overlaps of the first and the second object OBJ-1, OBJ-2 in hypothetical projection captures which are obtained from the at least one capture trajectory. Hypothetical projection captures are here determined by a simulated projection of the first and second three-dimensional object mask 3D-OBJM-1, 3D-OBJM-2 from the standpoint of the at least one capture trajectory. In particular, more than one hypothetical projection capture can be determined in this way for the at least one capture trajectory. The at least one capture trajectory here indicates a direction of the projection or the angle relative to the first and the second object OBJ-1, OBJ-2 from which projection captures can be generated from the standpoint of the capture trajectory. A degree or a proportion of the projective overlap between the first and the second object OBJ-1, OBJ-2 may be determined for each of these hypothetical projection captures. In particular, each of the hypothetical projection captures may comprise a plurality of pixels which are arranged in a two-dimensional pixel matrix. In particular, the number of pixels which map a projective overlap of the first and the second object OBJ-1, OBJ-2 can be determined in each of the hypothetical projection captures. The overlap OVL which is determined for the at least one capture trajectory may be the sum of the pixels of the projective overlaps of the individual hypothetical projection captures. In particular, this sum can be normalized by being divided by the number of hypothetical projection captures for which the projective overlap was determined. Alternatively, for example, an average degree of the projective overlaps from the hypothetical projection captures may be determined as overlap OVL. In other words, an average of the proportion of the projective overlap in the respective hypothetical projection images can be determined as the overlap OVL of the at least one capture trajectory.

In optional embodiments of the present invention, the capture trajectory for recording the three-dimensional medical image is dependent on the positioning of the object under examination UOBJ. The capture trajectory describes angles or capture angles or directions of view relative to the object under examination UOBJ from which projection captures for reconstructing the three-dimensional medical image are to be recorded. For this purpose, the imaging system for recording the projection images, in particular the X-ray system, must here adopt specific positions relative to the object under examination UOBJ. These positions are adopted as a result of the capture trajectory being traveled along. For this purpose, the imaging system, in particular the X-ray system, can travel along the capture trajectory by an adapted movement. Alternatively or additionally, the object under examination UOBJ can be correspondingly positioned or located relative to the imaging system, in particular the X-ray system. In particular, suitable positioning of the object under examination UOBJ can ensure that the imaging system can always travel along a fixed movement or permit only small differences from the fixed movement. Suitable positioning of the object under examination UOBJ relative to the imaging system, in particular the X-ray system, can then ensure that the desired capture trajectory relative to the object under examination UOBJ is actually traveled along.

In optional embodiments of the present invention, the object under examination can be immobilized in a positioning device to ensure suitable positioning. For example, the object under examination may be a human head. The head may then be immobilized in a head shell while the capture trajectory is traveled along. Using the head shell, it is possible to set and define a tilt and/or rotation of the head relative to the recording imaging system, in particular the X-ray system.

In optional embodiments of the present invention, segmenting SEG-1 of the first object OBJ-1 and segmenting SEG-2 of the second object OBJ-2 are based on thresholding. For this purpose, a first numerical range or value range may be defined for the first object OBJ-1. A second numerical range or value range may be defined for the second object OBJ-2. The first and the second numerical range may here be disjunctive. Alternatively, the first and the second numerical range may partially overlap. On segmentation SEG-1 of the first object OBJ-1, all the pixels in the exploratory views IMG-1, IMG-2 whose pixel values lie within the first numerical range are assigned to the first object OBJ-1. These pixels thus form the segmented first object OBJ-1 in the exploratory views IMG-1, IMG-2. As described above, one pixel of the first two-dimensional object masks 2D-OBJM-11, 2D-OBJM-21 corresponds to each pixel of the exploratory views IMG-1, IMG-2. In the first two-dimensional object masks 2D-OBJM-11, 2D-OBJM-21, a pixel value of one may then be assigned to those pixels which were assigned to the first object in the exploratory views IMG-1, IMG-2. All the other pixels of the first two-dimensional object masks 2D-OBJM-11, 2D-OBJM-21 can be assigned a pixel value of zero. Alternatively, the pixel values of zero and one can be swapped. The second two-dimensional object masks 2D-OBJM-12, 2D-OBJM-22 can be analogously determined in relation to the second numerical range.

In one optional embodiment of the present invention, on determination DET-1 of the first three-dimensional object mask 3D-OBJM-1, the first three-dimensional object mask 3D-OBJM-1 is determined by way of an unweighted backprojection of the first two-dimensional object masks 2D-OBJM-11, 2D-OBJM-21. In other words, the first two-dimensional object masks 2D-OBJM-11, 2D-OBJM-21 are "smudged back" in an unweighted manner in order to determine the first three-dimensional object mask 3D-OBJM-1. The second three-dimensional object mask 3D-OBJM-2 is determined analogously by way of unweighted backprojection of the second two-dimensional object masks 2D-OBJM-12, 2D-OBJM-22 in the method step of determining DET-2 the second three-dimensional object mask 3D-OBJM-2.

In optional embodiments of the present invention, in the method step of determining DET-1 the first three-dimensional object mask 3D-OBJM-1, the first three-dimensional object mask 3D-OBJM-1 is determined by way of segmentation, in particular by way of thresholding, from the backprojected first two-dimensional object masks. In other words, the first two-dimensional object masks 2D-OBJM-11, 2D-OBJM-21 are firstly backprojected by way of an unweighted backprojection into the three-dimensional space. Smudging may occur here. This backprojection of the first two-dimensional object masks 2D-OBJM-11, 2D-OBJM-21 is then segmented in order to determine the first three-dimensional object mask 3D-OBJM-1 from the backprojection. In this manner, smudging can be removed. The backprojection is here mapped by the backprojected first two-dimensional object masks 2D-OBJM-11, 2D-OBJM-21. Segmentation of the backprojection may in particular be based on thresholding. A threshold value may be defined for this purpose. The backprojection may here comprise a plurality of voxels which are arranged in a three-dimensional voxel matrix. A voxel value is assigned to each of these voxels as a function of the unweighted backprojection. The voxels whose voxel value is greater than or equal to the threshold value are segmented as belonging to the first object OBJ-1 in the first three-dimensional object mask 3D-OBJM-1. All other voxels can be segmented as not belonging to the object. Alternatively, the voxels whose voxel value is below the threshold value can be segmented as belonging to the first object OBJ-1. Alternatively, segmentation of the backprojected two-dimensional object masks may proceed by application of a trained function to the first two-dimensional object masks. The trained function can be trained to recognize and segment objects with a specific shape even if, under certain circumstances, they are mapped incompletely and/or in overlapped manner. In this manner, the trained function may be configured to correct a mapped shape of the first object OBJ-1 in accordance with the actual shape. The second three-dimensional object mask 3D-OBJM-2 can be determined analogously by segmentation of the backprojected first two-dimensional object masks or the backprojection of the first two-dimensional object masks 2D-OBJM-12, 2D-OBJM-22.

In optional embodiments of the present invention, precisely two exploratory views IMG-1, IMG-2 are provided in the method step of providing PROV-1 the exploratory views IMG-1, IMG-2. Accordingly, precisely two first two-dimensional object masks 2D-OBJM-11, 2D-OBJM-21 and precisely two second two-dimensional object masks 2D-OBJM-12, 2D-OBJM-22 are in each case also determined.

According to a further optional embodiment of the present invention, there is an angle of between 45° and 135° between the two exploratory views IMG-1, IMG-2. In particular, the angle between the two exploratory views IMG-1, IMG-2 is 90°. The angle between the two exploratory views IMG-1, IMG-2 is described by the angle which is enclosed by the angles or capture angles or viewing angles or directions of view of the two exploratory views IMG-1, IMG-2 onto the object under examination UOBJ.

FIG. 2 shows a second exemplary embodiment of a computer-implemented method for defining a capture trajectory for recording a first and a second object OBJ-1, OBJ-2 in a three-dimensional medical image.

The method steps of providing PROV-1 at least two exploratory views IMG-1, IMG-2, segmenting SEG-1 the first object OBJ-1, segmenting SEG-2 the second object OBJ-2, determining DET-1 the first three-dimensional object mask 3D-OBJM-1, determining DET-2 the second three-dimensional object mask 3D-OBJM-2 and determining DET-3 the overlap OVL of the first and the second object OBJ-1, OBJ-2 are configured analogously to the description in relation to FIG. 1.

According to the second exemplary embodiment, in the method step of determining DET-3 the overlap OVL for at least one capture trajectory, the overlap OVL is determined for more than one capture trajectory. Each of the capture trajectories here indicates a plurality of angles relative to the object under examination UOBJ from which hypothetical projection captures can be determined.

In a method step of determining DET-4 an optimum capture trajectory, the optimum capture trajectory is determined from the capture trajectories for which the overlap OVL was in each case previously determined. That capture trajectory which has the minimum overlap OVL is here determined as the optimum capture trajectory. In other words, the capture trajectory for which the smallest or least overlap OVL could be determined is the optimum capture trajectory.

In a method step of recording REC-1 the three-dimensional medical image, the three-dimensional medical image is recorded as a function of the optimum capture trajectory. The three-dimensional medical image is here recorded by the optimum capture trajectory relative to the object under examination UOBJ being traveled along. The optimum capture trajectory may here be set or traveled along by an adapted movement of the imaging system, in particular of the X-ray system, and/or by suitable positioning of the object under examination UOBJ.

FIG. 3 shows a third exemplary embodiment of a computer-implemented method for defining a capture trajectory for recording a first and a second object OBJ-1, OBJ-2 in a three-dimensional medical image.

The method steps of providing PROV-1 at least two exploratory views IMG-1, IMG-2, segmenting SEG-1 the first object OBJ-1, segmenting SEG-2 the second object OBJ-2, determining DET-1 the first three-dimensional object mask 3D-OBJM-1, determining DET-2 the second three-dimensional object mask 3D-OBJM-2 and determining DET-3 the overlap OVL of the first and the second object OBJ-1, OBJ-2 are configured analogously to the description in relation to FIG. 1. The method steps of determining DET-4 the optimum capture trajectory and of recording REC-1 the three-dimensional medical image are configured according to the description in relation to FIG. 2.

As already described according to FIG. 1, the object under examination UOBJ can be positioned or immobilized by way of a positioning device. The object under examination is here immobilized by the positioning relative to the imaging system, in particular relative to the X-ray system.

As described above, the positioning device may in particular be a head shell which is configured to accommodate a patient's head. The patient's head is here the object under examination UOBJ. The first and the second object are here arranged in the head. The head shell is configured to set a rotation and/or tilt of the head.

The positioning device may here be automatically actuatable. The positioning of the object under examination UOBJ can be automatically adapted in this manner.

In a method step of positioning POS the object under examination UOBJ, the object under examination UOBJ is positioned relative to the imaging system, in particular relative to the X-ray system, in accordance with the optimum capture trajectory. The positioning device is here automatically actuated as a function of the optimum capture trajectory such that the object under examination UOBJ is positioned in accordance with the positioning for the optimum capture trajectory.

In particular, positioning POS of the object under examination UOBJ may be adapted such that the imaging system, in particular the X-ray system, can travel along a standard trajectory. The object under examination UOBJ is here positioned such that the standard trajectory corresponds to the optimum capture trajectory relative to the object under examination UOBJ.

Alternatively, in addition to positioning, the movement of the imaging system, in particular of the X-ray system, i.e. the trajectory traveled along by the imaging system, may be adapted to the positioning of the object under examination UOBJ. In this manner, it is possible on the basis of the combination of the positioning and the adapted movement of the imaging system to ensure that the imaging system travels along the optimum capture trajectory around the object under examination UOBJ.

FIG. 4 shows a fourth exemplary embodiment of a computer-implemented method for defining a capture trajectory for recording a first and a second object OBJ-1, OBJ-2 in a three-dimensional medical image.

The method steps of providing PROV-1 at least two exploratory views IMG-1, IMG-2, segmenting SEG-1 the first object OBJ-1, segmenting SEG-2 the second object OBJ-2, determining DET-1 the first three-dimensional object mask 3D-OBJM-1, determining DET-2 the second three-dimensional object mask 3D-OBJM-2 and determining DET-3 the overlap OVL of the first and the second object OBJ-1, OBJ-2 are configured analogously to the description in relation to FIG. 1. The method steps of determining DET-4 the optimum capture trajectory and of recording REC-1 the three-dimensional medical image are configured according to the description in relation to FIG. 2. The method step of positioning POS the object under examination UOBJ can be configured according to the description in relation to FIG. 3.

The method step of recording REC-1 the three-dimensional medical image comprises a method step of recording REC-2 a plurality of two-dimensional projection captures of the object under examination UOBJ along the optimum capture trajectory. The angles or capture angles or viewing angles from which a projection capture can be recorded are here restricted relative to the object under examination UOBJ by the optimum capture trajectory.

At least two projection captures are here recorded from varying angles. In particular, all the projection captures can be recorded from varying angles.

In particular, a projection capture can be recorded at regular intervals while the capture trajectory is being traveled along. The phrase "regular intervals" may here refer to regularity in time and/or space. In particular, projection captures of the object under examination UOBJ can be recorded in regular angular steps. In other words, the imaging system, in particular the X-ray system, can move onward along the optimum capture trajectory by a specific angular step between the recording of two projection captures.

The method step of recording REC-1 the three-dimensional medical image moreover comprises a method step of reconstructing RECO the three-dimensional medical image as a function of the plurality of two-dimensional projection captures. The three-dimensional medical image can here be reconstructed with a known reconstruction algorithm. For example, the three-dimensional medical image can be reconstructed on the basis of the two-dimensional projection images by way of filtered backprojection.

A metal artifact correction may optionally be carried out on reconstruction of the three-dimensional medical image. For example, metal artifact correction can be carried out as described in Meyer, Esther, et al. "Normalized metal artifact reduction (NMAR) in computed tomography." Medical Physics 37.10 (2010): 5482-5493.

FIG. 5 shows a fifth exemplary embodiment of a computer-implemented method for defining a capture trajectory for recording a first and a second object OBJ-1, OBJ-2 in a three-dimensional medical image.

The method steps of providing PROV-1 at least two exploratory views IMG-1, IMG-2, segmenting SEG-1 the first object OBJ-1, segmenting SEG-2 the second object OBJ-2, determining DET-1 the first three-dimensional object mask 3D-OBJM-1, determining DET-2 the second three-dimensional object mask 3D-OBJM-2 and determining DET-3 the overlap OVL of the first and the second object OBJ-1, OBJ-2 are configured analogously to the description in relation to FIG. 1. The method steps of determining DET-4 the optimum capture trajectory and of recording REC-1 the three-dimensional medical image are configured according to the description in relation to FIG. 2. The method step of positioning POS the object under examination UOBJ can be configured according to the description in relation to FIG. 3. The method steps of recording REC-2 a plurality of two-dimensional projection captures and of reconstructing RECO the three-dimensional medical image are configured according to the description in relation to FIG. 4.

According to the fifth exemplary embodiment the method step of segmenting SEG-1 the first object OBJ-1 comprises a method step of applying APP-1 a first trained function to the exploratory views IMG-1, IMG-2. The first two-dimensional object masks 2D-OBJM-11, 2D-OBJM-21 are here determined. The first two-dimensional object masks 2D-OBJM-11, 2D-OBJM-21 are here configured as described with regard to FIG. 1. The first trained function is here trained to segment the first object OBJ-1 in the exploratory views.

In particular, the first trained function can segment the first object OBJ-1 on the basis of the pixel values of the exploratory views IMG-1, IMG-2 in a similar manner to thresholding.

Alternatively or additionally, the first trained function can be specifically configured for segmenting the first object OBJ-1. For this purpose, the first trained function can be trained for the shape or spatial extent of the first object OBJ-1. The first object OBJ-1 can in this case have a typical shape which all first objects OBJ-1 have in this application. The first trained function can be trained to recognize and segment precisely this shape. The first trained function may here be configured to completely segment the first object OBJ-1 even if it is only partially mapped or is overlapped by another object or an artifact in at least one exploratory view IMG-1, IMG-2. In other words, the first trained function may be configured to correct the shape of the mapped first object OBJ-1. In other words, the first trained function may be configured to segment the first object OBJ-1 in its complete shape in the exploratory views IMG-1, IMG-2 even if only some of the first object OBJ-1 is correctly mapped in the exploratory views IMG-1, IMG-2 due to an overlap.

According to the fifth exemplary embodiment, the method step of segmenting SEG-2 the second object OBJ-2 comprises a method step of applying APP-2 a second trained function to the exploratory views IMG-1, IMG-2. The second trained function is here configured analogously to the description relating to the first trained function only in relation to the second object OBJ-2. In particular, the second trained function may be configured to recognize and segment a typical shape of the second object OBJ-2.

In some embodiments of the present invention, it is also possible for only one of the method steps of segmenting SEG-1 the first object OBJ-1 and of segmenting SEG-2 the second object OBJ-2 to be carried out by application APP-1, APP-2 of one of the trained functions.

FIG. 6 is a schematic representation of a data stream on performance of the first exemplary embodiment of a computer-implemented method for defining a capture trajectory for recording a first and a second object OBJ-1, OBJ-2 in a three-dimensional medical image.

At least one part of an exemplary data stream on performance of the method described in FIGS. 1 to 5 is depicted.

In exploratory views IMG-1, IMG-2, which are provided in the method step of providing PROV-1 at least two exploratory views IMG-1, IMG-2, the object under examination UOBJ, in which the first and the second object OBJ-1, OBJ-2 are arranged, is mapped. In the example depicted, the object under examination UOBJ is a patient's head. The first and the second object OBJ-1, OBJ-2 are arranged in the object under examination UOBJ, thus in the head. According to the exemplary depiction, the first object OBJ-1 is a coil package which is of isotropic, i.e. directionally independent, configuration. The second object OBJ-2 is a stent, the mapping of which is at least partially overlapped by the first object OBJ-1 in the exploratory views IMG-1, IMG-2. For better depiction, the first and the second object OBJ-1, OBJ-2 are highlighted in exploratory views IMG-1, IMG-2.

In the method step of segmenting SEG-1 the first object OBJ-1, the first object OBJ-1 in the exploratory views is segmented as described in FIGS. 1 to 5. The first two-dimensional object masks 2D-OBJM-11, 2D-OBJM-21 are here determined. In the first two-dimensional object masks 2D-OBJM-11, 2D-OBJM-21, a pixel value of one is assigned to the pixels which map the first object OBJ-1 in the exploratory views IMG-1, IMG-2 or in which the first object OBJ-1 was mapped without overlap. All the other pixels of the first two-dimensional object masks 2D-OBJM-11, 2D-OBJM-21 are assigned a pixel value of zero.

Analogously, in the method step of segmenting SEG-2 the second object OBJ-2, the second object OBJ-2 in the exploratory views IMG-1, IMG-2 is segmented. The second two-dimensional object masks 2D-OBJM-12, 2D-OBJM-22 are here determined. The second two-dimensional object masks 2D-OBJM-12, 2D-OBJM-22 are configured analogously to the first two-dimensional object masks 2D-OBJM-11, 2D-OBJM-21 only in relation to the second object OBJ-2.

In the method step of determining DET-1 the first three-dimensional object mask 3D-OBJM-1, the first three-dimensional object mask 3D-OBJM-1 of the first object OBJ-1 is determined as a function of the first two-dimensional object masks 2D-OBJM-11, 2D-OBJM-21. In particular, the first three-dimensional object mask 3D-OBJM-1 can be determined by unweighted backprojection of the first two-dimensional object masks 2D-OBJM-11, 2D-OBJM-21. Moreover, as described according to FIG. 1, segmentation, in particular thresholding, can additionally be carried out to determine the first three-dimensional object mask 3D-OBJM-1. The first three-dimensional object mask 3D-OBJM-1 here describes the shape or spatial extent of the first object OBJ-1, and its position in space.

Analogously, in the method step of determining DET-2 the second three-dimensional object mask 3D-OBJM-2, the second three-dimensional object mask 3D-OBJM-2 is determined as a function of the second two-dimensional object masks 2D-OBJM-12, 2D-OBJM-22. The second three-dimensional object mask 3D-OBJM-2 may here be determined analogously to the first three-dimensional object mask 3D-OBJM-1. The second three-dimensional object mask 3D-OBJM-2 then describes the shape or spatial extent of the second object OBJ-2, and the position of the second object OBJ-2 in space.

As a function of the first and the second three-dimensional object mask 3D-OBJM-1, 3D-OBJM-2, in the method step of determining DET-3 the overlap OVL of the first and the second object OBJ-1, OBJ-2 is determined for at least one capture trajectory. In particular, the overlap OVL can be determined for a plurality of capture trajectories. For this purpose, hypothetical projection captures from angles predetermined by the capture trajectory relative to the first and the second object OBJ-1, OBJ-2 are simulated for each of the capture trajectories. The overlap OVL can then, as described according to FIG. 1, in each case be determined in the hypothetical projection captures for the different capture trajectories. The projective overlaps for different hypothetical projection captures are here by way of example depicted in the grid by different shades of gray. The capture trajectory for which the overlap OVL is comparatively the least can be determined as the optimum capture trajectory.

FIG. 7 shows an exemplary embodiment of a computer-implemented training method for providing a first and/or second trained function.

The training method is described below jointly for both the first and the second trained function, since the two functions are trained analogously. The first function is trained only in relation to the first object OBJ-1 and the data obtained therefrom, while the second function is trained in relation to the second object OBJ-2 and the data obtained therefrom.

First input data are received in a method step of receiving TREC-11 and second input data in a method step of receiving TREC-21. The first and the second input data here comprise exploratory views IMG-1, IMG-2 which are configured as described with regard to FIG. 1. In particular, the first input data maps at least the first object OBJ-1 and the second input data maps at least the second object OBJ-2.

First output data is received in a method step of receiving TREC-12 and second output data in a method step of receiving TREC-22. The first output data here comprises first two-dimensional object masks 2D-OBJM-11, 2D-OBJM-21. The second output data here comprises second two-dimensional object masks 2D-OBJM-12, 2D-OBJM-22. The first and second two-dimensional object masks 2D-OBJM-11, 2D-OBJM-21, 2D-OBJM-12, 2D-OBJM-22 are here configured according to the description in relation to FIG. 1. In particular, a first or second two-dimensional object mask 2D-OBJM-11, 2D-OBJM-21, 2D-OBJM-12, 2D-OBJM-22 is assigned to each exploratory view IMG-1, IMG-2.

In particular, a first and a second two-dimensional object mask 2D-OBJM-11, 2D-OBJM-21, 2D-OBJM-12, 2D-OBJM-22 can in each case be manually determined by an expert for each exploratory view IMG-1, IMG-2 of the first or second input data. In particular, a skilled person can for this purpose segment the first or second object OBJ-1, OBJ-2 in the exploratory views. In other words, the skilled person segments the first object OBJ-1 in the first input data to generate the first output data and the second object OBJ-2 in the first input data to generate the second output data. The skilled person may, for example, be a physician, in particular a radiologist.

In a training method step TRAIN-1 a first function is trained on the basis of the first input data and the first output data and in a training method step TRAIN-2 a second function is trained on the basis of the second input data and the second output data.

The first or second function is here applied to the first or second input data respectively. First or second specific determined output data are here in each case accordingly determined. This first or second determined output data determined in this manner is respectively compared with the previously received first or second output data. On the basis of this comparison, at least one parameter of the first or second function is adapted such that, on renewed application of the first or second function to the first or second input data, the first or second output data determined in this manner is a better match for the received first or second output data. In this manner, the first or second function is trained by iterative adaptation of the at least one parameter and the first or second trained function is thus determined.

Adaptation can be repeated iteratively until a termination criterion is met. The termination criterion may for example be exceedance of a maximum, predefined number of iterations and/or undershooting of a maximum, predefined deviation between the determined and the received first or second output data etc.

The first trained function is provided in a providing method step TPROV-1 and the second trained function is provided in a providing method step TPROV-2. The first or second trained function is here in particular provided such that it can be applied or used for the method described according to FIG. 5.

FIG. 8 shows a determination system SYS for defining a capture trajectory for recording a first and a second object OBJ-1, OBJ-2 in a three-dimensional medical image; FIG. 9 shows a first or second training system TSYS-1, TSYS-2 for providing a first and/or second trained function.

The depicted determination system SYS for defining a capture trajectory for recording a first and a second object OBJ-1, OBJ-2 in a three-dimensional medical image is configured to carry out a method, according to one or more example embodiments of the present invention, for defining a capture trajectory for recording a first and a second object OBJ-1, OBJ-2 in a three-dimensional medical image. The depicted first or second training system TSYS-1, TSYS-2 respectively is configured to carry out a method according to one or more example embodiments of the present invention for providing the first and/or second trained function. The first and the second training system TSYS-1, TSYS-2 are here configured analogously to one another. The determination system SYS comprises an interface SYS.IF, a computing unit SYS.CU and a memory unit SYS.MU. The first or second training system TSYS-1, TSYS-2 respectively comprises a first or second training interface TSYS-1.IF, TSYS-2.IF, a first or second training computing unit TSYS-1.CU, TSYS-2.CU and a first or second training memory unit TSYS-1.MU, TSYS-2.MU.

The determination system SYS and/or the first or second training system TSYS-1, TSYS-2 may in particular be a computer, a microcontroller or an integrated circuit (IC). Alternatively, the determination system SYS and/or the first or second training system TSYS-1, TSYS-2 may be a real or virtual computer network (a technical term for a real computer network is "cluster" and a technical term for a virtual computer network is "cloud"). The determination system SYS and/or the first or second training system TSYS-1, TSYS-2 may be configured as a virtual system which is run on a computer or a real computer network or a virtual computer network (a technical term is "virtualization").

The interface SYS.IF and/or the first or second training interface TSYS-1.IF, TSYS-2.IF may be a hardware or software interface (e.g. a PCI bus, USB or FireWire). The computing unit SYS.CU and/or the first or second training computing unit TSYS-1.CU, TSYS-2.CU may comprise hardware and/or software components, for example a microprocessor or a field programmable gate array (FPGA). The memory unit SYS.MU and/or the first or second training memory unit TSYS-1.MU, TSYS-2.MU may be configured as a volatile working memory (random access memory, RAM) or as a non-volatile mass storage device (hard disk, USB stick, SD card, solid state disk (SSD)).

The interface SYS.IF and/or the first or second training interface TSYS-1.IF, TSYS-2.IF may in particular comprise a plurality of subinterfaces which carry out different method steps of the respective method according to one or more example embodiments of the present invention. In other words, the interface SYS.IF and/or the first or second training interface TSYS-1.IF, TSYS-2.IF may be configured as a plurality of interfaces SYS.IF and/or first or second training interfaces TSYS-1.IF, TSYS-2.IF. The computing unit SYS.CU and/or the first or second training computing unit TSYS-1.CU, TSYS-2.CU may in particular comprise a plurality of subcomputing units which carry out different method steps of the respective method according to one or more example embodiments of the present invention. In other words, the computing unit SYS.CU and/or the first or second training computing unit TSYS-1.CU, TSYS-2.CU may be configured as a plurality of computing units SYS.CU and/or first or second training computing units TSYS-1.CU, TSYS-2.CU.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where it has not yet been explicitly done but is reasonable and in line with the purposes of the present invention, individual exemplary embodiments, individual sub-aspects or features thereof can be combined with one another or swapped without going beyond the scope of the present invention. Advantages of the present invention described in relation to one exemplary embodiment also apply, where transferable, to other exemplary embodiments without being explicitly stated to do so.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A computer-implemented method for defining a capture trajectory for recording a first object and a second object in a three-dimensional medical image, the first object and the second object being arranged in an object under examination, and the computer-implemented method comprising:

providing at least two exploratory views of the first object and the second object, wherein the at least two exploratory views map the first object and the second object from different angles;

segmenting the first object in the at least two exploratory views to determine first two-dimensional object masks;

segmenting the second object in the at least two exploratory views to determine second two-dimensional object masks;

determining a first three-dimensional object mask of the first object as a function of the first two-dimensional object masks;

determining a second three-dimensional object mask of the second object as a function of the second two-dimensional object masks; and determining an overlap of the first object and the second object for at least one capture trajectory for recording the three-dimensional medical image as a function of the first three-dimensional object mask and the second three-dimensional object mask, wherein the overlap is determined from projected overlaps of the first object and the second object in simulated projection captures obtained from the at least one capture trajectory.

2. The computer-implemented method as claimed in claim 1, wherein the three-dimensional medical image and the at least two exploratory views are recorded and provided by way of an X-ray system.

3. The computer-implemented method as claimed in claim 2, wherein a first absorption coefficient of the first object is greater than a second absorption coefficient of the second object.

4. The computer-implemented method as claimed in claim 1, wherein the at least one capture trajectory is dependent on positioning of the object under examination.

5. The computer-implemented method as claimed in claim 1, wherein the determining the overlap of the first object and the second object is carried out for at least two capture trajectories.

6. The computer-implemented method as claimed in claim 5, further comprising:

determining an optimum capture trajectory, wherein the optimum capture trajectory is a capture trajectory corresponding to a minimum overlap of the first object and the second object; and recording the three-dimensional medical image as a function of the optimum capture trajectory.

7. The computer-implemented method as claimed in claim 6, wherein the object under examination is positioned by way of a positioning device, wherein, prior to recording the three-dimensional medical image, the computer-implemented method includes positioning the object under examination in accordance with the optimum capture trajectory, and wherein the positioning device is automatically actuated as a function of the optimum capture trajectory such that the object under examination is positioned in accordance with the positioning for the optimum capture trajectory.

8. The computer-implemented method as claimed in claim 6, wherein the three-dimensional medical image is recorded with an X-ray system, and wherein the X-ray system travels along the optimum capture trajectory during recording the three-dimensional medical image.

9. The computer-implemented method as claimed in claim 6, wherein the recording the three-dimensional medical image comprises:
   recording a plurality of two-dimensional projection captures of the object under examination along the optimum capture trajectory, wherein at least two two-dimensional projection captures are recorded from varying angles; and
   reconstructing the three-dimensional medical image as a function of the plurality of two-dimensional projection captures, wherein a metal artifact correction is carried out during reconstruction of the three-dimensional medical image.

10. The computer-implemented method as claimed in claim 1,
   wherein the segmenting the first object and the segmenting the second object are based on thresholding.

11. The computer-implemented method as claimed in claim 1, wherein at least one of
   the segmenting the first object includes applying a first trained function to the at least two exploratory views to determine the first two-dimensional object masks, or
   the segmenting the second object includes applying a second trained function to the at least two exploratory views to determine the second two-dimensional object masks.

12. The computer-implemented method as claimed in claim 1, wherein at least one of
   the first three-dimensional object mask is determined by way of an unweighted backprojection of the first two-dimensional object masks, or
   the second three-dimensional object mask is determined by way of an unweighted backprojection of the second two-dimensional object masks.

13. The computer-implemented method as claimed in claim 12, wherein at least one of
   the first three-dimensional object mask is determined by way of segmentation of the backprojected first two-dimensional object masks, or
   the second three-dimensional object mask is determined by way of segmentation of the backprojected second two-dimensional object masks.

14. The computer-implemented method as claimed in claim 1,
   wherein at least one of the first object is a coil package or the second object is a stent.

15. The computer-implemented method as claimed in claim 1,
   wherein the providing provides only two exploratory views.

16. The computer-implemented method as claimed in claim 15,
   wherein an angle between the two exploratory views is between 45° and 135°, and
   wherein the angle between the two exploratory views is in particular 90°.

17. The computer-implemented method as claimed in claim 7, wherein the recording the three-dimensional medical image comprises:
   recording a plurality of two-dimensional projection captures of the object under examination along the optimum capture trajectory, wherein at least two two-dimensional projection captures are recorded from varying angles; and
   reconstructing the three-dimensional medical image as a function of the plurality of two-dimensional projection captures, wherein a metal artifact correction is carried out during reconstruction of the three-dimensional medical image.

18. The computer-implemented method as claimed in claim 8, wherein the recording the three-dimensional medical image comprises:
   recording a plurality of two-dimensional projection captures of the object under examination along the optimum capture trajectory, wherein at least two two-dimensional projection captures are recorded from varying angles; and
   reconstructing the three-dimensional medical image as a function of the plurality of two-dimensional projection captures, wherein a metal artifact correction is carried out during reconstruction of the three-dimensional medical image.

19. The computer-implemented method as claimed in claim 3,
   wherein the determining the overlap of the first object and the second object is carried out for at least two capture trajectories.

20. A determination system for defining a capture trajectory for recording a first object and a second object in a three-dimensional medical image, the first object and the second object being arranged in an object under examination, and the determination system comprising:
   an interface configured to provide at least two exploratory views of the first object and the second object, wherein the at least two exploratory views map the first object and the second object from different angles; and
   a computing unit configured to
      segment the first object in the at least two exploratory views to determine first two-dimensional object masks,
      segment the second object in the at least two exploratory views to determine second two-dimensional object masks,
      determine a first three-dimensional object mask of the first object as a function of the first two-dimensional object masks,
      determine a second three-dimensional object mask of the second object as a function of the second two-dimensional object masks,
      determine an overlap of the first object and the second object for at least one capture trajectory for recording the three-dimensional medical image as a function of the first three-dimensional object mask and the second three-dimensional object mask, wherein the overlap is determined from projected overlaps of the first object and the second object in simulated projection captures obtained from the at least one capture trajectory.

21. A non-transitory computer-readable storage medium on storing computer-executable instructions that, when executed at a determination system, cause the determination system to perform the method of claim 1.

* * * * *